United States Patent
Rogers et al.

(10) Patent No.: US 11,721,432 B1
(45) Date of Patent: Aug. 8, 2023

(54) MEDICATION INVENTORY SYSTEM INCLUDING BOUNDARY OUTLINE BASED MEDICATION TRAY STOCKING LIST AND RELATED METHODS

(71) Applicant: INMAR Rx SOLUTIONS, INC., Ft. Worth, TX (US)

(72) Inventors: Brian S. Rogers, Greensboro, NC (US); James W. McCracken, Jr., Lewisville, NC (US); Seth Maxwell, Lewisville, NC (US); Patrick S. Connelly, Carnegie, PA (US); Justin A. Krull, Hurst, TX (US); Jared O. Santibanez, Forney, TX (US); Greg J. Brendel, West Mifflin, PA (US)

(73) Assignee: INMAR RX SOLUTIONS, INC., Ft. Worth, TX (US)

( * ) Notice: Subject to any disclaimer, the term of this patent is extended or adjusted under 35 U.S.C. 154(b) by 88 days.

(21) Appl. No.: 17/162,781

(22) Filed: Jan. 29, 2021

Related U.S. Application Data

(63) Continuation-in-part of application No. 16/793,098, filed on Feb. 18, 2020, which is a continuation-in-part
(Continued)

(51) Int. Cl.
*A61J 1/03* (2023.01)
*G06V 10/44* (2022.01)
(Continued)

(52) U.S. Cl.
CPC .............. *G16H 40/20* (2018.01); *A61J 1/03* (2013.01); *G06V 10/44* (2022.01); *G06V 10/50* (2022.01);
(Continued)

(58) Field of Classification Search
CPC ........ G16H 40/20; G16H 20/10; G16H 70/40; A61J 1/03; A61J 2205/10; A61J 2205/50; G06V 10/44; G06V 10/50; G06V 20/10
See application file for complete search history.

(56) References Cited

U.S. PATENT DOCUMENTS

| | | |
|---|---|---|
| 3,069,654 A | 12/1962 | Hough |
| 4,768,661 A | 9/1988 | Pfeifer |

(Continued)

FOREIGN PATENT DOCUMENTS

| | | | | |
|---|---|---|---|---|
| EP | 1089229 A2 | * | 4/2001 | ........... G06K 9/6253 |
| WO | WO-2017220868 A1 | * | 12/2017 | ......... G06K 9/00127 |

OTHER PUBLICATIONS

Duda et al., "Use of Hough Transformation to Detect Lines and Curves" (Year: 1972).*
(Continued)

*Primary Examiner* — Thien T Mai
(74) *Attorney, Agent, or Firm* — Allen, Dyer, Doppelt + Gilchrist, P.A.

(57) ABSTRACT

A medication inventory system may include a medication tray that includes compartments for storing respective medications. The medication tray may have a tray identifier associated therewith. The system may also include a mobile wireless communications device configured to obtain at least one image of the medication tray, and apply a Hough line detection algorithm to the at least one image to determine a boundary outline of the medication tray. The mobile wireless communications device may also be configured to generate a current medication stocking list of the medication tray based upon the boundary outline and the tray identifier from the at least one image.

25 Claims, 28 Drawing Sheets

Related U.S. Application Data of application No. 16/704,573, filed on Dec. 5, 2019, now Pat. No. 11,462,312.

(51) Int. Cl.
  *G16H 20/10* (2018.01)
  *G16H 40/20* (2018.01)
  *G16H 70/40* (2018.01)
  *G06V 10/50* (2022.01)
  *G06V 20/10* (2022.01)

(52) U.S. Cl.
  CPC .............. *G06V 20/10* (2022.01); *G16H 20/10* (2018.01); *G16H 70/40* (2018.01); *A61J 2205/10* (2013.01); *A61J 2205/50* (2013.01)

(56) References Cited

U.S. PATENT DOCUMENTS

| | | | |
|---|---|---|---|
| 6,332,285 | B1 | 12/2001 | Aaldenberg et al. |
| 7,085,432 | B2 | 8/2006 | Paquette |
| 7,599,516 | B2 | 10/2009 | Limer et al. |
| 8,861,816 | B2 | 10/2014 | Lang et al. |
| 8,966,863 | B2 | 3/2015 | Amano et al. |
| 9,757,305 | B2 | 9/2017 | Ika et al. |
| 9,910,965 | B2 | 3/2018 | Bufalini et al. |
| 10,083,366 | B2 | 9/2018 | Song et al. |
| 10,357,428 | B2 | 7/2019 | Ika et al. |
| 11,030,752 | B1 * | 6/2021 | Backlund ................ G06T 7/194 |
| 2007/0239482 | A1 | 10/2007 | Finn et al. |
| 2010/0027845 | A1 | 2/2010 | Kim et al. |
| 2012/0069383 | A1 | 3/2012 | Hines et al. |
| 2012/0319550 | A1 | 12/2012 | Manniso et al. |
| 2013/0070090 | A1 | 3/2013 | Bufalini et al. |
| 2013/0091679 | A1 | 4/2013 | Gloger et al. |
| 2014/0042229 | A1 | 2/2014 | Tsai et al. |
| 2014/0214438 | A1 | 7/2014 | Ahmadi |
| 2014/0288952 | A1 | 9/2014 | Smith et al. |
| 2016/0147976 | A1 * | 5/2016 | Jain ....................... G16H 20/10 705/2 |
| 2016/0364686 | A1 | 12/2016 | Wolfe et al. |
| 2017/0098049 | A1 | 4/2017 | Sweeney |
| 2017/0246083 | A1 | 8/2017 | Amano et al. |
| 2017/0270508 | A1 | 9/2017 | Roach et al. |
| 2018/0260665 | A1 | 9/2018 | Zhang et al. |
| 2019/0333008 | A1 | 10/2019 | Wolfe et al. |
| 2020/0296062 | A1 | 9/2020 | Wilson |
| 2021/0298994 | A1 * | 9/2021 | Liu ....................... G16H 80/00 |
| 2022/0008291 | A1 | 1/2022 | Grosfils et al. |

OTHER PUBLICATIONS

Acero et al., "How the Hough Transform Was Invented" (Year: 2009).*

McCracken, Jr. et al., U.S. Appl. No. 16/395,343, filed Apr. 26, 2019.

McCracken, Jr. et al., U.S. Appl. No. 16/395,353, filed Apr. 26, 2019.

Rogers et al., U.S. Appl. No. 16/704,573, filed Dec. 5, 2019.

Rogers et al., U.S. Appl. No. 16/793,098, filed Feb. 18, 2020.

* cited by examiner

MEDICATION INVENTORY SYSTEM INCLUDING BOUNDARY OUTLINE BASED MEDICATION TRAY STOCKING LIST AND RELATED METHODS

RELATED APPLICATIONS

The present application is a continuation-in-part of U.S. patent application Ser. No. 16/793,098, filed Feb. 18, 2020, which is a continuation-in-part of U.S. patent application Ser. No. 16/704,573, filed Dec. 5, 2019, the entire contents of both are hereby incorporated by reference.

TECHNICAL FIELD

The present invention relates to the field of medicine, and, more particularly, to medication inventory systems and related methods.

BACKGROUND

Medications, including controlled substances, medical devices, and/or medical tools may be relatively important for treatment of a patient. Thus, it may be desirable to maintain medications in a relatively orderly and predictable fashion to reduce the amount of time it takes to access these medications, particularly in a time sensitive situation.

A medication tray is often used to provide a specific selection and quantity of medications for a particular medical use case, physician preference, and/or location. A given health care facility may have multiple variations of medication trays in use, each varying in type, amount, and/or placement of medications within the medication tray. Multiple medication trays may be used within a crash cart, which is a wheeled cart for dispensing of medication (e.g., in an emergency). Consequently, health care facility pharmacies may process and manage a relatively large quantity of medication trays used throughout a facility.

Accordingly, the medication trays are typically managed. Contents of the medication trays may be replenished and verified, for example, between uses. The verification may be performed manually and include inspection for recalled, expired, and misplaced medications.

U.S. Patent Application Publication No. 2017/0246083 to Amano et al. is directed to a medicine sorting apparatus. More particularly, Amano et al. discloses a medicine sorting apparatus that includes an identifying part, e.g., based upon a camera, which can identify a direction, a posture and characteristics such as a shape, a size, a type and an expiration date of a medicine, and a storing part for storing the medicine so that the medicine can be taken from the storing part. A determination processing part can determine whether or not the medicine is a target to be treated based on the characteristics of the medicine identified by the identifying part.

U.S. Patent Application Publication No. 2018/0260665 to Zhang et al. is directed to a deep learning system for recognizing pills in images. More particularly, the system and method use deep learning, including convolutional neural networks, to identify subject objects in unconstrained user images such as unknown pills. An image of, e.g., a pill, may be captured and subsequently processed using deep learning models to identify the pill. The deep learning models may be optimized to have a small footprint (in terms of computational and memory resources) suitable for a resource-limited device such as a smartphone while retaining a high object recognition accuracy. Each such model may also be run on modified versions of the unconstrained image, for example on color, greyscale, and gradient images, to focus the models on different distinguishing features of the object.

SUMMARY

A medication inventory system may include a medication tray that includes a plurality of compartments for storing respective medications. The medication tray may have a tray identifier associated therewith. The medication inventory system may include a mobile wireless communications device configured to obtain at least one image of the medication tray, and apply a Hough line detection algorithm to the at least one image to determine a boundary outline of the medication tray. The mobile wireless communications device may also be configured to generate a current medication stocking list of the medication tray based upon the boundary outline and the tray identifier from the at least one image.

The mobile wireless communications device may be configured to split the at least one image into a plurality of image segments and apply the Hough line detection algorithm to each of the plurality of image segments to determine the boundary outline of the medication tray, for example. The mobile wireless communications device may be configured to detect a plurality of edges of the medication tray within the at least one image of the medication tray, generate a plurality of edge images based upon the detected plurality of edges, and apply the Hough line detection algorithm to each of the plurality of detected edge images to determine the boundary outline of the medication tray.

The mobile wireless communications device may be configured to identify corners of the boundary outline of the medication tray based upon the Hough line detection algorithm. The mobile wireless communications device may be configured to obtain a plurality of images of the medication tray and apply the Hough line detection algorithm to the plurality of images to determine the boundary outline of the medication tray, for example.

The plurality of images of the medication tray may include a plurality of images of the medication tray having different fields of view relative to the medication tray. The mobile wireless communications device may be configured to determine the boundary outline of the medication tray based upon the different fields of view, for example.

The mobile wireless communications device may be configured to determine a desired medication stocking list for the medication tray based upon the tray identifier. The mobile wireless communications device may be configured to determine at least one missing medication based upon the current medication stocking list and the desired medication stocking list, for example.

Each medication may have a respective medication identifier associated therewith, for example. The mobile wireless communications device may be configured to determine expired medications within the medication tray based upon the medication identifiers, and generate and communicate an expiration notification based thereon. The mobile wireless communications device may be configured to determine medications within the medication tray within a threshold time from expiration based upon the medication identifiers, and generate and communicate an expiration notification based thereon.

A method aspect is directed to a method of processing medication inventory in a medication inventory system comprising a medication tray that includes a plurality of compartments for storing respective medications. The medication tray may have a tray identifier associated therewith. The method may include using a mobile wireless communications device to obtain at least one image of the medication tray, and apply a Hough line detection algorithm to the at least one image to determine a boundary outline of the medication tray. The method may also include using the mobile wireless communications device to generate a current medication stocking list of the medication tray based upon the boundary outline and the tray identifier from the at least one image.

A computer readable medium aspect is directed to a non-transitory computer readable medium for a medication inventory system that includes a medication tray including a plurality of compartments for storing respective medications, the medication tray having a tray identifier associated therewith. The non-transitory computer readable medium includes computer executable instructions that when executed by a controller of a mobile wireless communications device cause the controller to perform operations. The operations may include obtaining at least one image of the medication tray, and applying a Hough line detection algorithm to the at least one image to determine a boundary outline of the medication tray. The operations may also include generating a current medication stocking list of the medication tray based upon the boundary outline and the tray identifier from the at least one image.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime and multiple prime notation are used to indicate similar elements in alternative embodiments.

Figure 1:
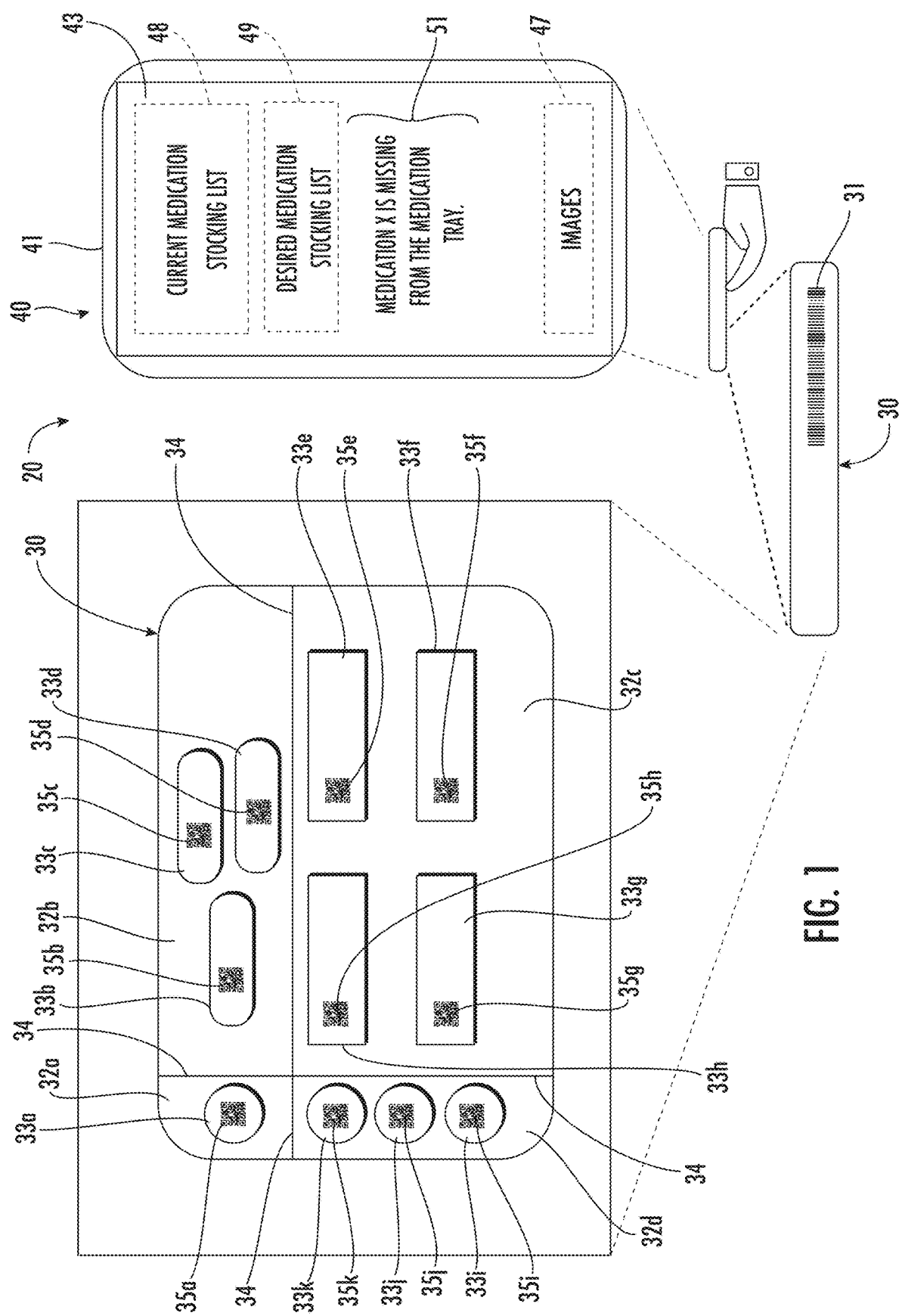
FIG. 1 is a schematic diagram of a medication inventory system in accordance with an embodiment.
Figure 2:
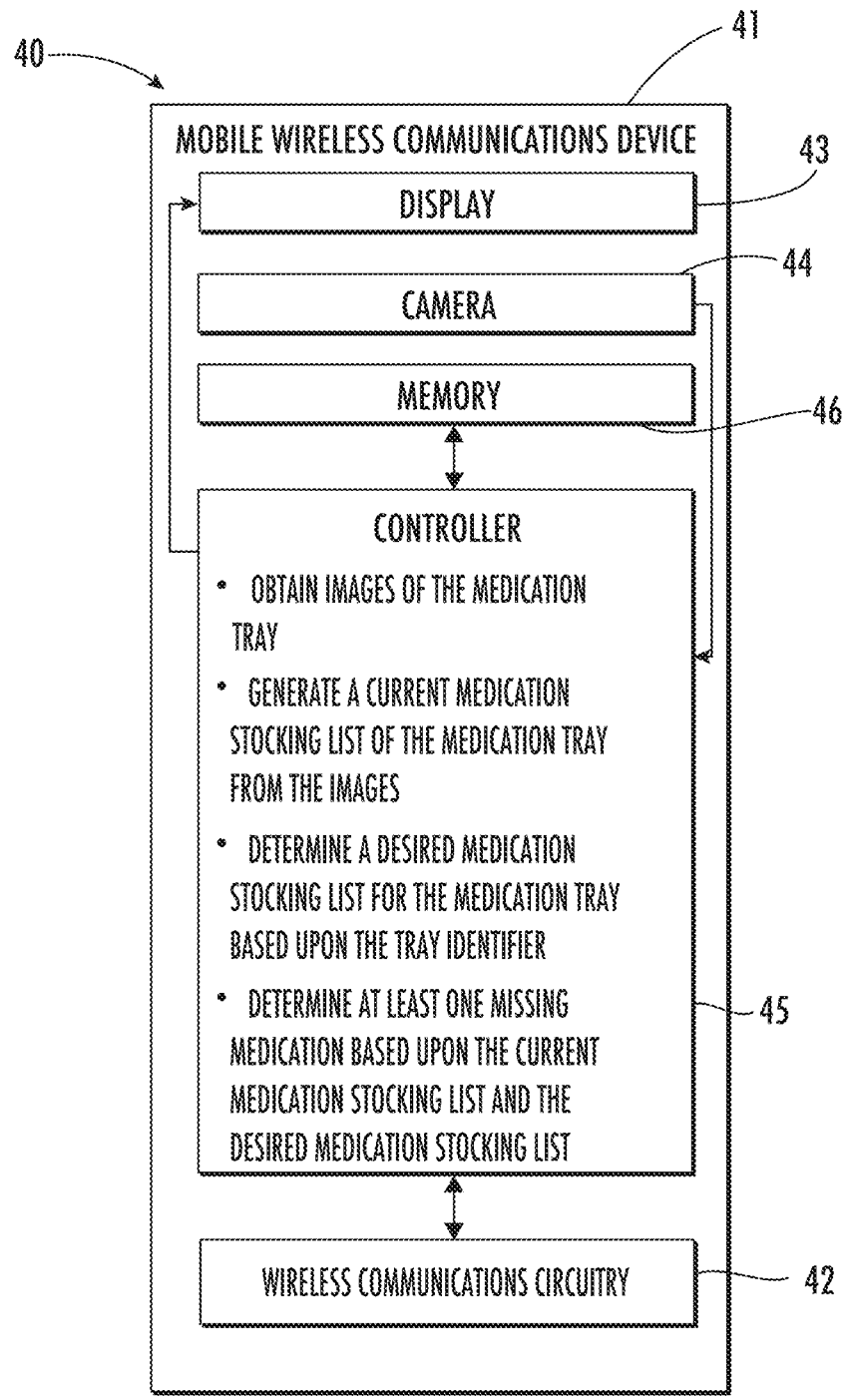
FIG. 2 is a schematic block diagram of the medication inventory system of FIG. 1.

Referring initially to FIGS. 1 and 2, a medication inventory system 20 illustratively includes a medication tray 30. The medication tray 30 includes partitions 34 that define compartments 32a-32n. Each compartment may store a medication 33a-33n, multiple medications, a medical or medicated device, a medication container that includes individual medications therein, or other item or substance used for medical treatment. For example, the medication tray 30 may be part of a crash cart, as will be appreciated by those skilled in the art. Of course, the medication tray 30 may be used in other medical environments, for example, an examination room, emergency room, treatment room, operating room, etc. For example, the medication tray 30 may be in the form of a drawer within a medication cabinet or medication dispensing cabinet. Each medication 33a-33n has a respective medication identifier 35a-35n associated therewith, for example, a barcode, quick-response (QR) code, alphanumeric characters, or other optically recognizable and unique code.

The medication tray 30 has a tray identifier 31 associated therewith. The tray identifier 31 may be in the form of a barcode, for example, that may be printed or applied (e.g., via an adhesive label) on the medication tray 30. The tray identifier 31 may be in the form of another type of identifier, for example, QR code, alphanumeric characters, or other optically recognizable and unique code.

The medication inventory system 20 also includes a mobile wireless communications device 40, illustratively in the form of a smartphone. The mobile wireless communications device 40 illustratively includes a housing 41 and wireless communications circuitry 42 carried by the housing. The mobile wireless communications device 40 also includes a display 43, for example, a touch display, carried by the housing 41. A controller 45 is coupled to the wireless communications circuitry 42 and the display 43. A camera 44 is also carried by the housing 41 and coupled to the controller 45. One or more input devices may be carried by the housing 41 and coupled to the controller 45. While the mobile wireless communications device 40 is illustratively in the form of a smartphone, the mobile wireless communications device may be in the form of a tablet, laptop computer, or wearable device, for example.

Figure 3:
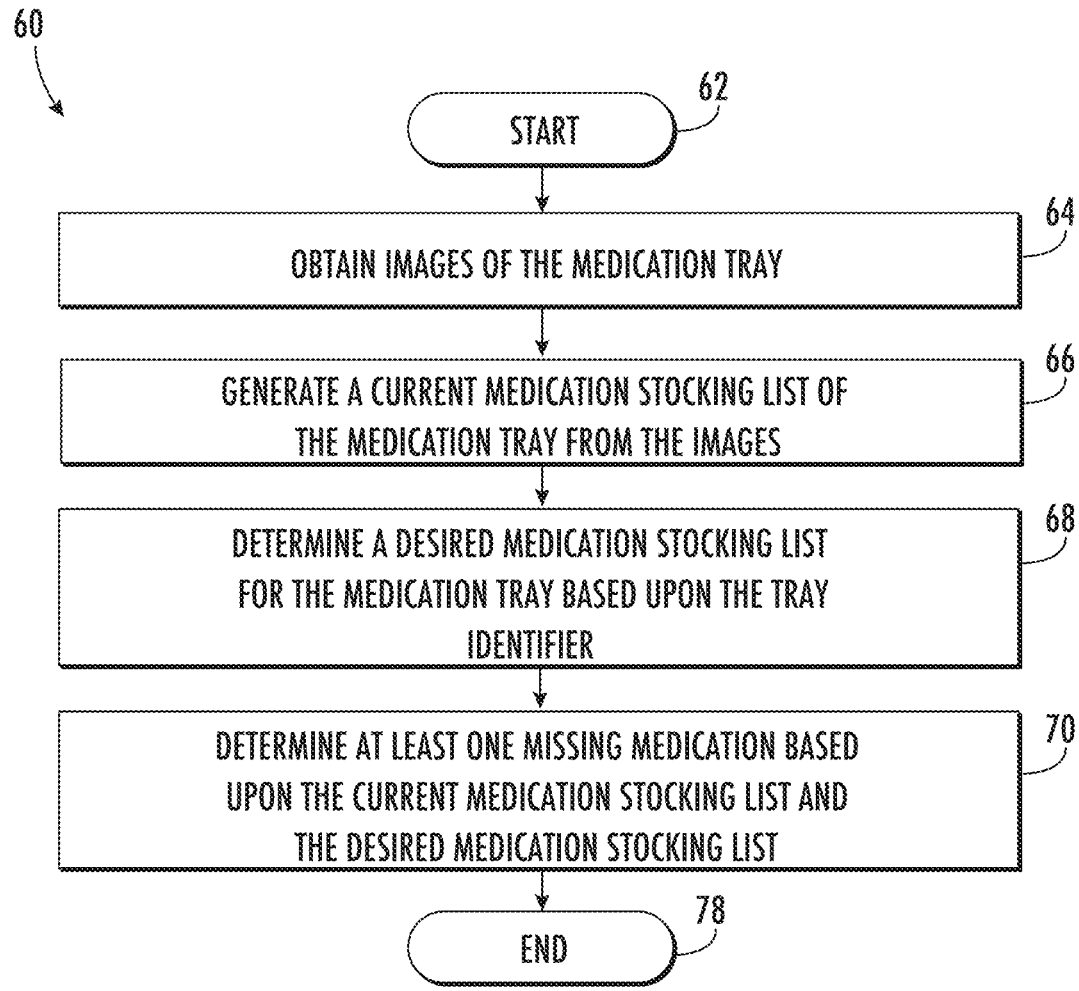
FIG. 3 is a flow diagram illustrating operation of the mobile wireless communications device of FIG. 2.
Figure 4:
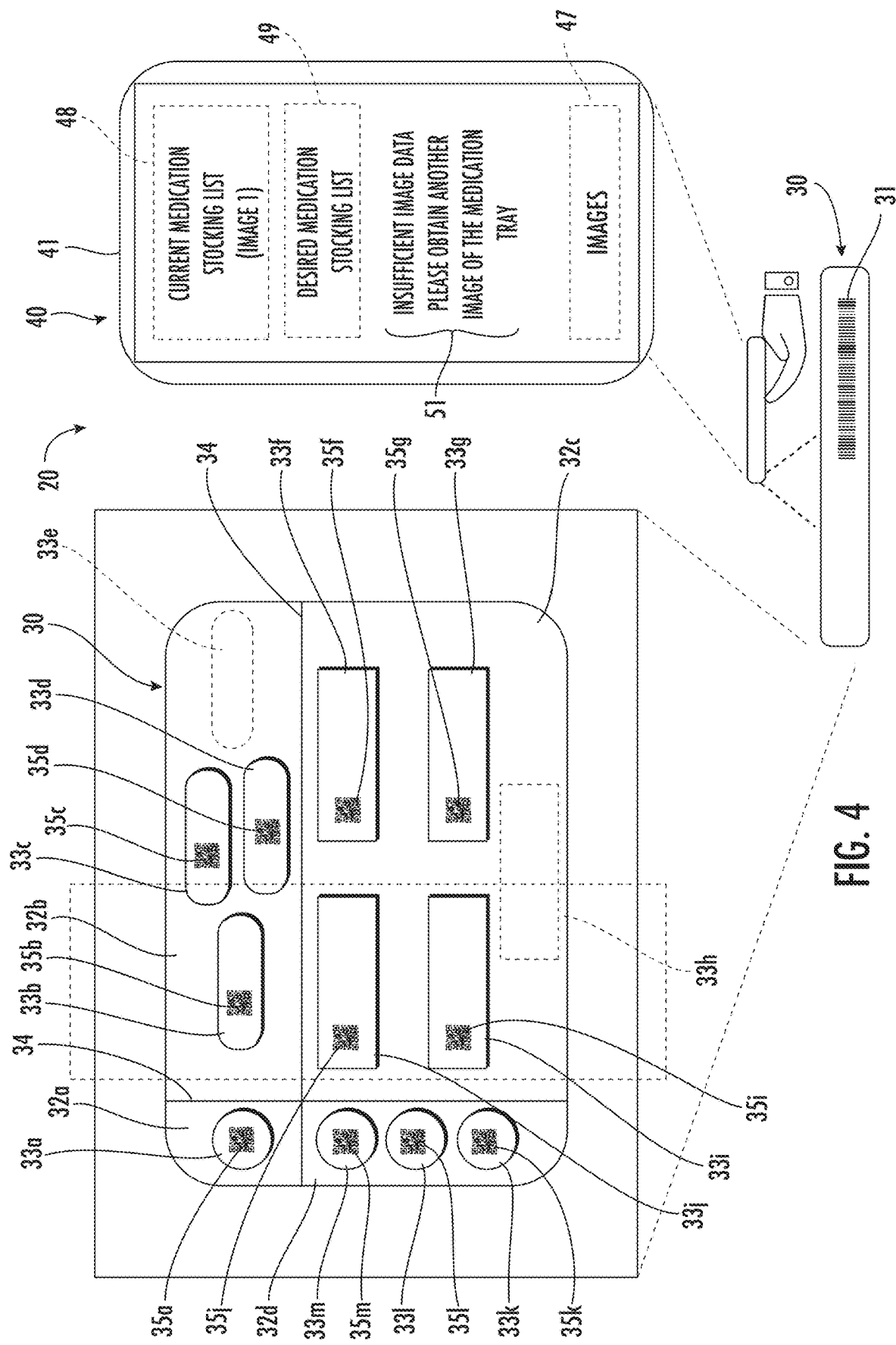
FIG. 4 is a schematic diagram of a medication inventory system in accordance with an embodiment.

Referring now additionally to the flowchart 60 in FIG. 3, beginning at Block 62, operations of the mobile wireless communications device 40 of the medication inventory system 20 will now be described. While operations of the mobile wireless communications device 40 are described, it will be appreciated by those skilled in the art that the controller 45 and an associated memory 46 cooperate to perform the operations.

At Block 64, the mobile wireless communications device 40 obtains images 47 of the medication tray 30. At Block 66, the mobile wireless communications device 40 generates a current medication stocking list 48 of the medication tray from the images 47.

The mobile wireless communications device 40 determines a desired medication stocking list 49 of the medication tray 30 based upon the tray identifier 31 (Block 68). More particularly, the mobile wireless communications device 40 may obtain the desired medication stocking list 49 from a remote computer or database based upon the tray identifier 31. In other words, the tray identifier 31 may be used as an index to retrieve or obtain the desired medication stocking list 49.

The mobile wireless communications device 40, at Block 70, determines one or more missing medications 33$a$-33$n$ based upon the current medication stocking list 48 and the desired medication stocking list 49. More particularly, if a medication 33$a$-33$n$ that is part of the desired medication stocking list 49 is determined to not be in the current medication stocking list 48 (i.e., a medication was not found in the images 47), a notification 51 may be generated and displayed on the display 43 of the mobile wireless communications device 40. The controller 45 may use image recognition techniques, for example, for identifying the medication identifiers 35$a$-35$n$, to determine missing medications. Operations end at Block 78.

Figure 8:
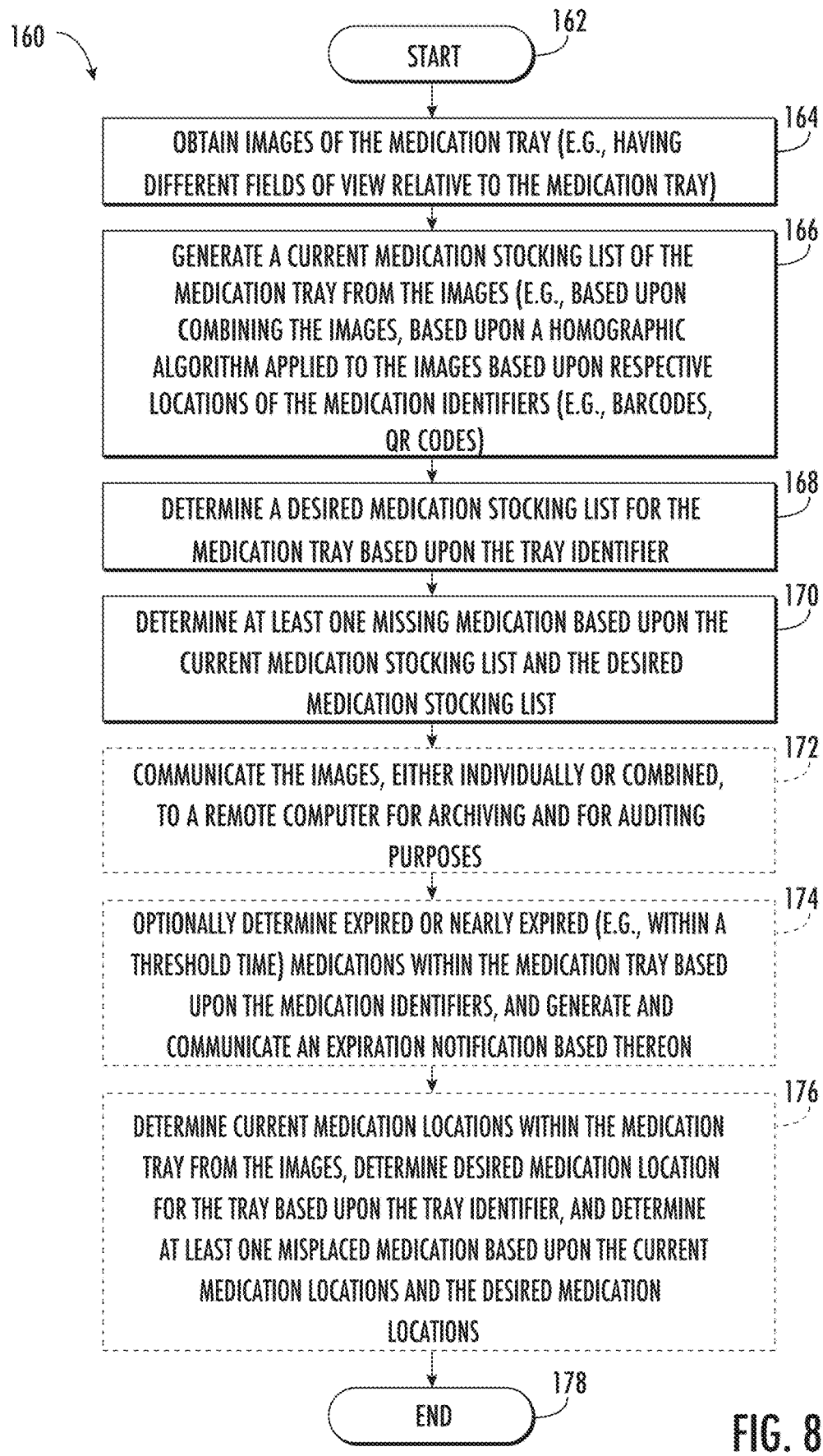
FIG. 8 is a flow diagram illustrating operation of the mobile wireless communications device of FIG. 4.

Referring now to FIGS. 4-7, and the flowchart 160 in FIG. 8, beginning at Block 162 more detailed operations of the mobile wireless communications device 40 with respect to the medication inventory system 20 will now be described. At Block 164, the mobile wireless communications device 40 obtains images 47 of the medication tray 30. The images 47 may include images having different fields of view relative to the medication tray 30. In other words, a given user may capture, via the camera 44, images of the medication tray 30. The images 47 may partially capture the medication tray 30. As will be appreciated by those skilled in the art, to obtain a high enough resolution to read both the tray and medication identifiers 31, 35, it may be desirable to position the mobile wireless communications device 40 including the camera 44 relatively close to the medication tray 30. As a result, a given image 47 may include only a portion of the medication tray 30 and thus not all medications 33$a$-33$n$ would be in the field of view.

Figure 5:
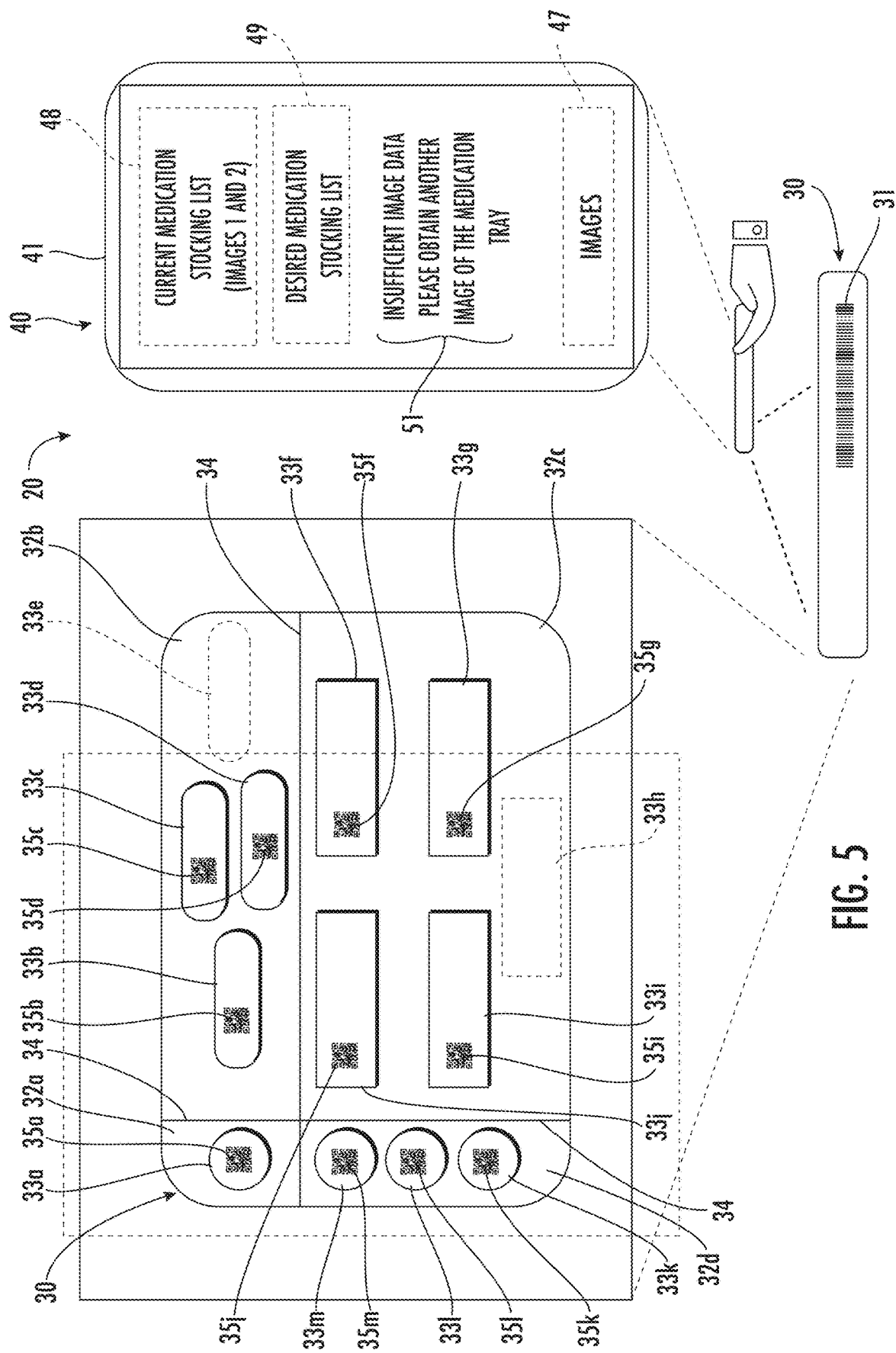
FIG. 5 is another schematic diagram of the medication inventory system in accordance with the embodiment of FIG. 4.
Figure 6:
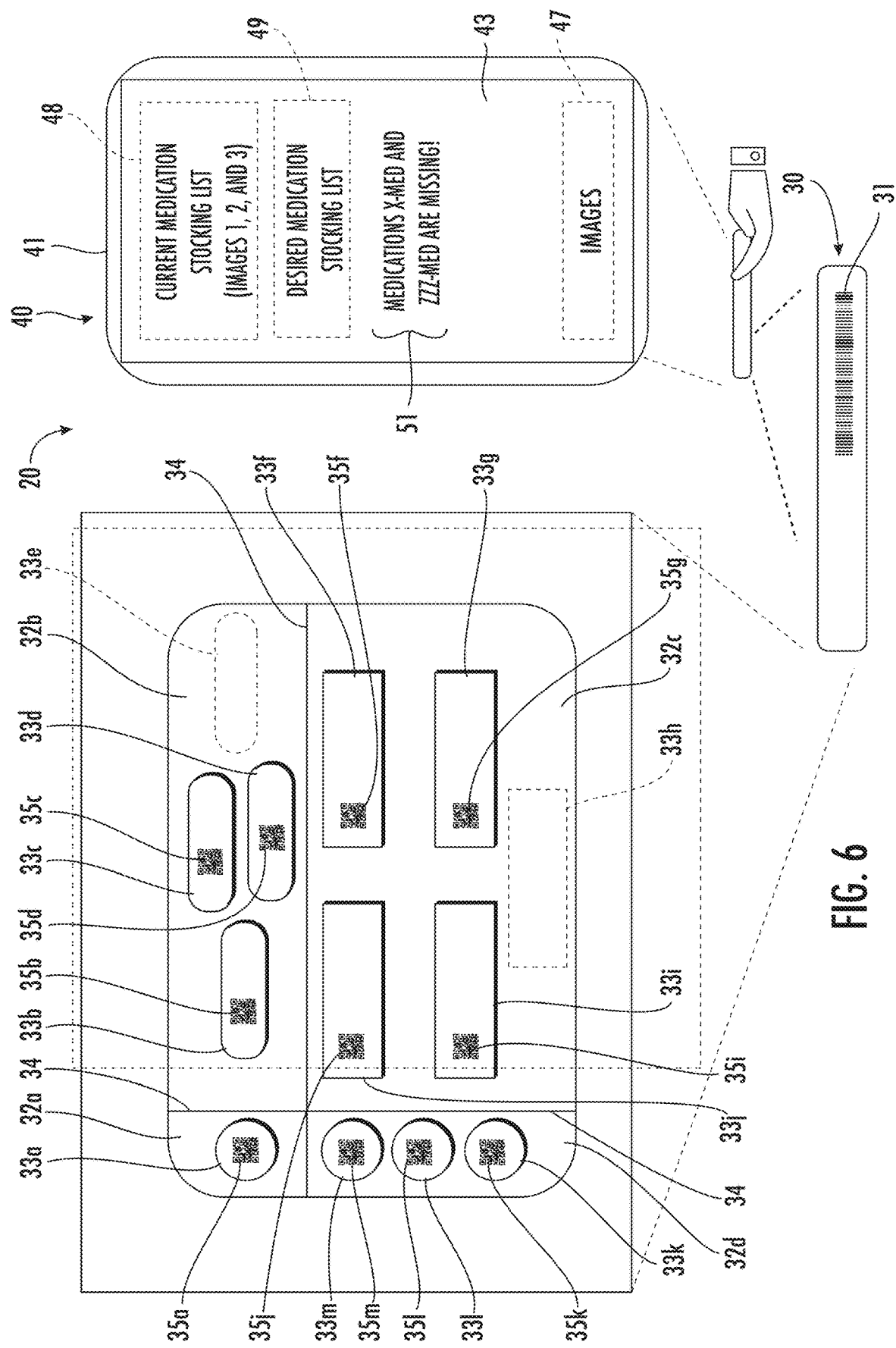
FIG. 6 is another schematic diagram of the medication inventory system in accordance with the embodiment of FIG. 4.
Figure 7:
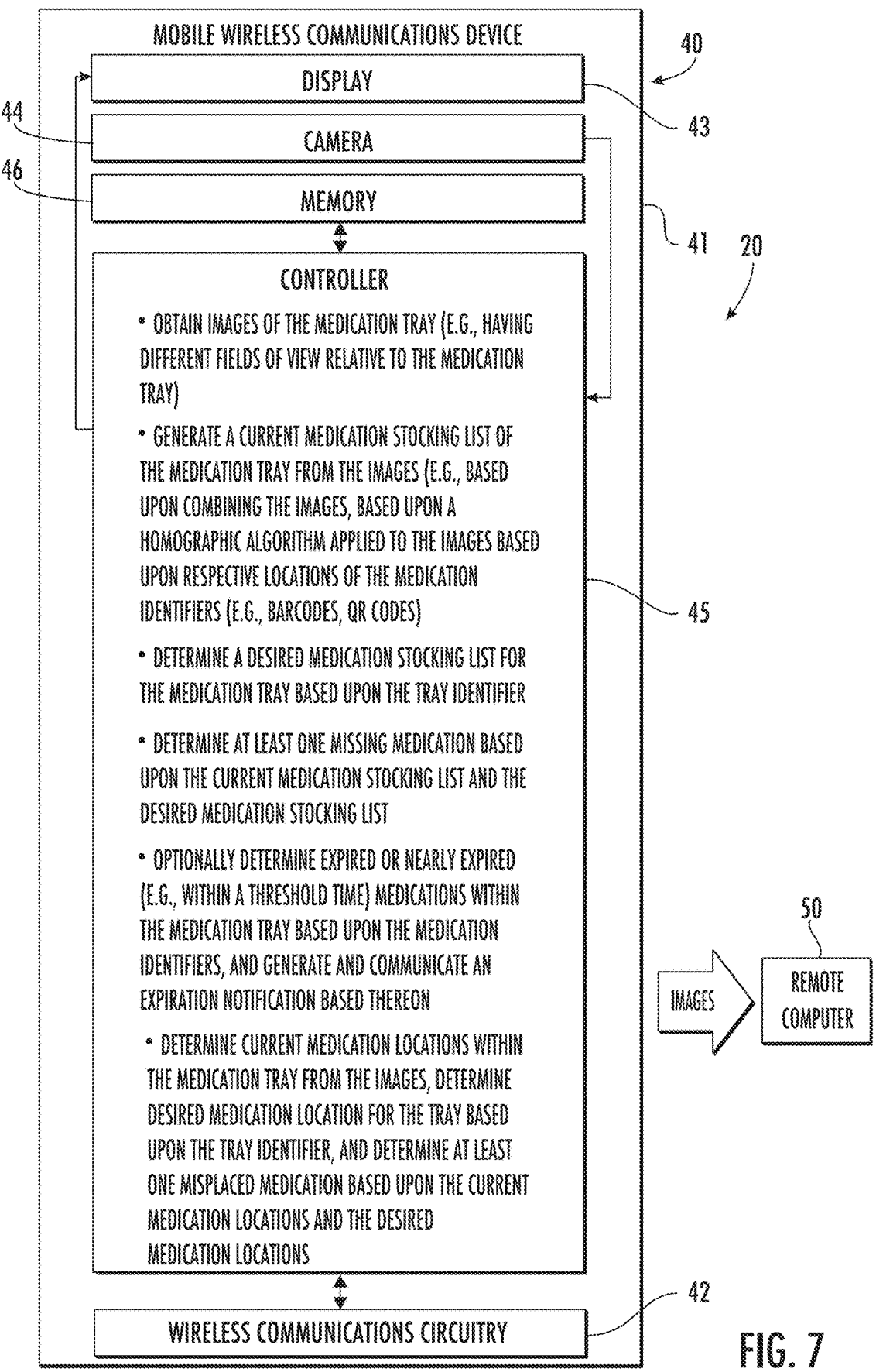
FIG. 7 is a schematic block diagram of the medication inventory system of FIG. 4.
Figure 9:
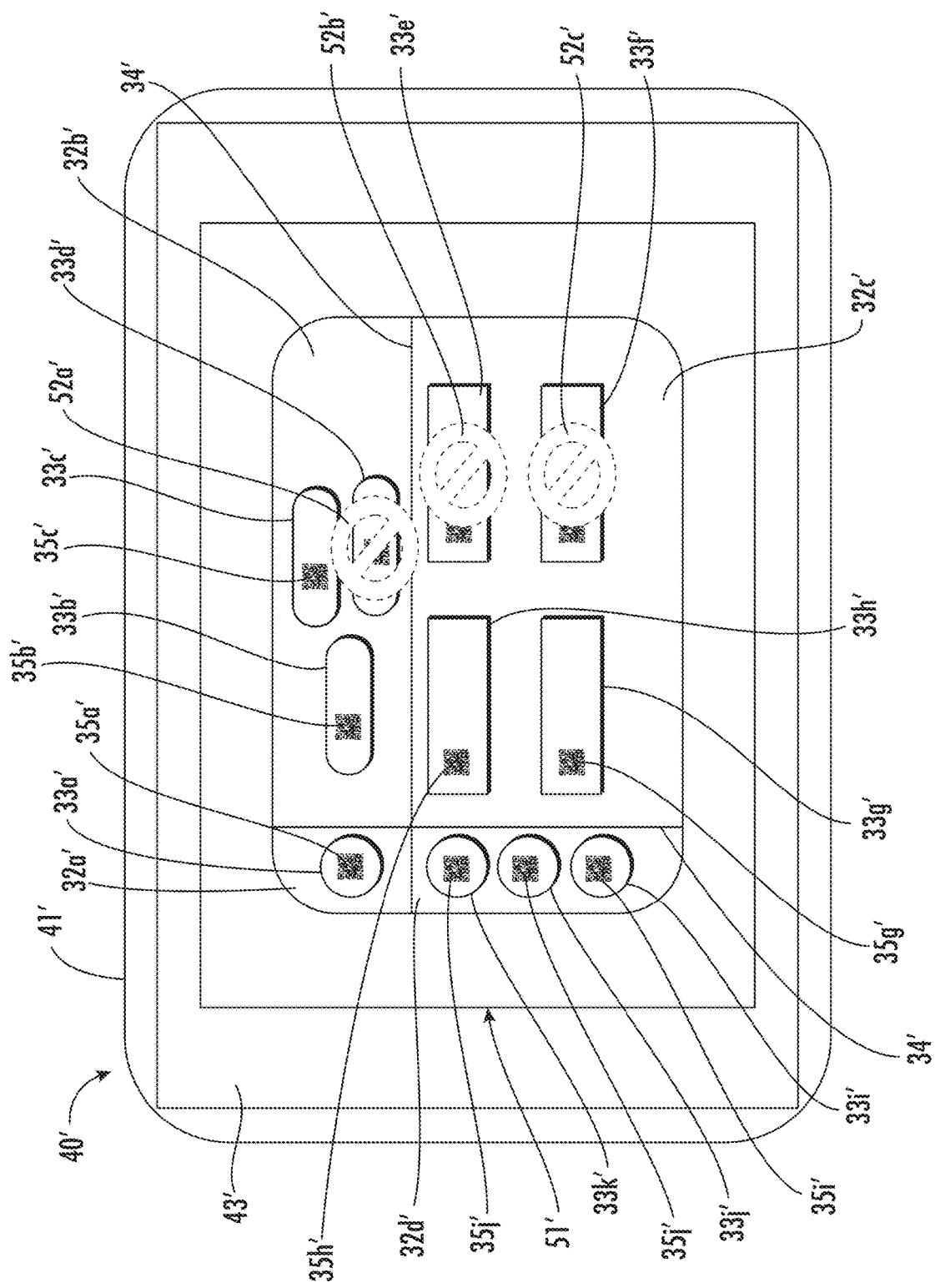
FIG. 9 is a schematic diagram of a mobile wireless communications device in accordance with another embodiment.

Moreover, a relative orientation of the mobile wireless communications device 40 to the medication tray 30 may result in some medication identifiers 35$a$-35$n$ not being able to be read or decoded. Thus, the mobile wireless communications device 40 may generate a notification 51 as to whether a sufficient number of images has been obtained (FIGS. 5-6). Referring briefly to FIG. 9, in another embodiment, the notification 51' may be in the form of an image of the medication tray 30' on the display 43' of the mobile wireless communications device 40' and include indicia 52$a'$-52$c'$, which may be color-coded, adjacent respective medications 33$d'$-33$f'$ for which medication identifiers 35$d'$-35$f'$ were unable to be identified or decoded.

At Block 166, the mobile wireless communications device 40 generates a current medication stocking list 48 of the medication tray 30 from the images 47. More particularly, the mobile wireless communications device 40 generates the current medication stocking list 48 based upon combining the images 47. For example, the mobile wireless communications device 40 may generate the current medication stocking list 48 based upon a homographic algorithm applied to the images 47, which may be based upon respective locations of the medication identifiers 35$a$-35$n$. An exemplary homographic algorithm, contrary to conventional homographic algorithms, does not use feature extraction or k-nearest-neighbor matching to provide the feature matches, but uses the individually identifiable identifiers (e.g., barcodes) already present in the process to provide feature matches, and as a result creates relatively consistent repeatable homographic processed images.

The mobile wireless communications device 40 determines a desired medication stocking list 49 of the medication tray 30 based upon the tray identifier 31 (Block 168), for example, using techniques along the lines described above. In some embodiments, desired medication stocking lists 49 for respective medication trays 30 may be stored in the memory 46 of the mobile wireless communications device 40.

The mobile wireless communications device 40, at Block 170, determines one or more missing medications 33$e$, 33$h$ (e.g., that may have been used) based upon the current medication stocking list 48 and the desired medication stocking list 49. More particularly, if a medication that is part of the desired medication stocking list 49 is determined to not be in the current medication stocking list 48 (i.e., a medication 33$e$, 33$h$ was not found in the combined images 47), a notification 51 may be generated and displayed on the display 43 of the mobile wireless communications device 40 and/or communicated. The notification 51 may be in the form of a list, for example, and/or an image of the medication tray with indicia (e.g. color-coded). The controller 45 may use image recognition techniques, for example, for identifying the medication identifiers 35$a$-35$n$, to determine missing medications. In some embodiments, the mobile wireless communications device 40 may determine that a medication is missing based upon there being less than a desired number (e.g., a threshold number) of medications in a given compartment.

In some embodiments, the mobile wireless communications device 40 may wirelessly communicate the images 47, either individually or combined, to a remote computer 50 for archiving and for auditing purposes (Block 172). The missing medications may also be wirelessly communicated to the remote computer 50. In some embodiments, the mobile wireless communications device 40 may generate and communicate an invoice for the missing medications. Alternatively or additionally, the mobile wireless communications device 40 may communicate the missing medications to a remote computer 50 for processing, for example, generation and communication of the invoices.

Figure 10:
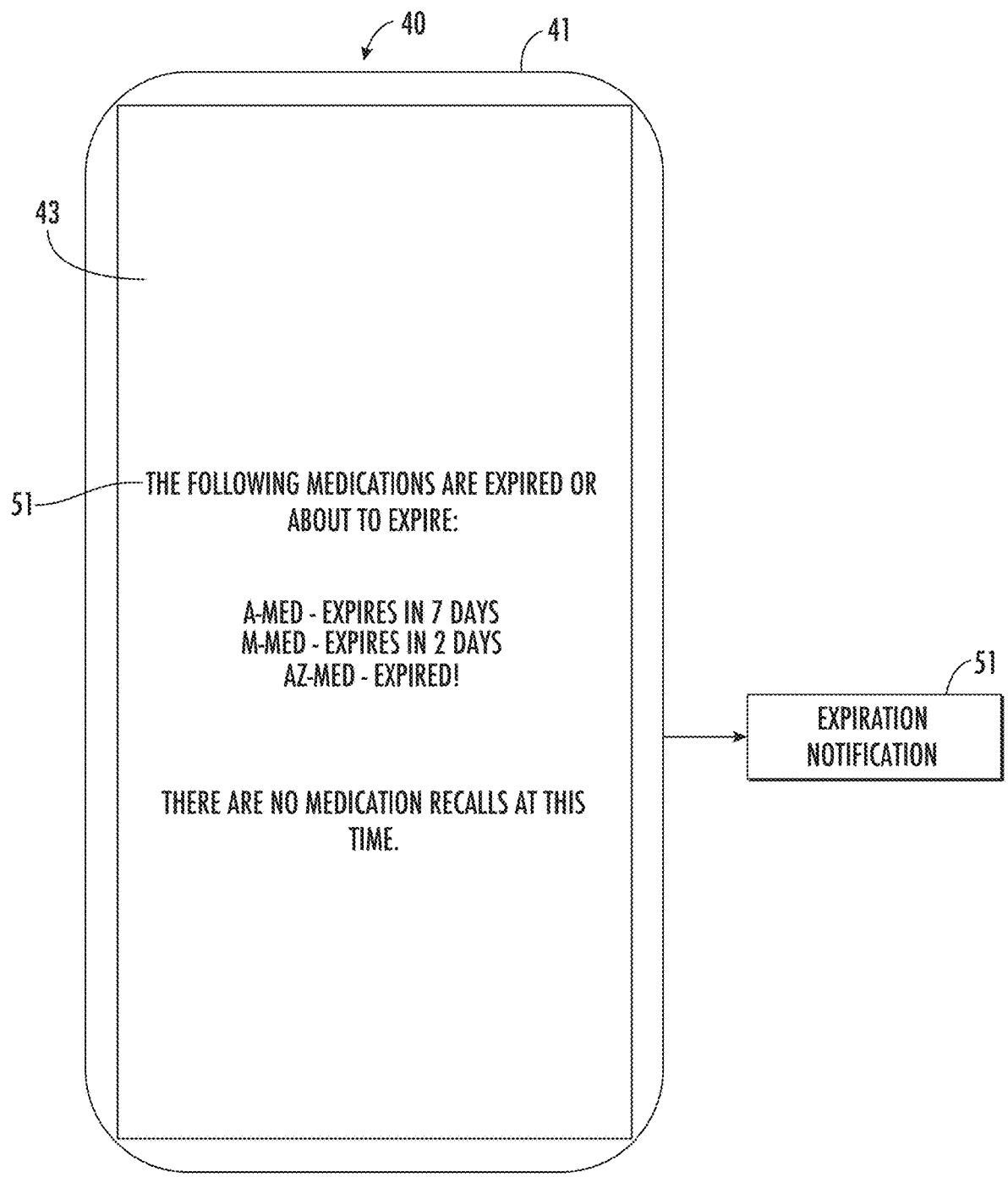
FIG. 10 is a schematic diagram of a mobile wireless communications device in accordance with an embodiment.

Referring now additionally to FIG. 10, the mobile wireless communications device 40 may also determine expired medications 33a-33n or nearly expired medications within the medication tray 30 based upon the medication identifiers 35a-35n (Block 174), for example, by comparing a lot number of the medication. The mobile wireless communications device 40 may generate an expiration notification 51 for display on the display 43 indicative of an expired medication or nearly expired medication (e.g., within a threshold time period from an actual expiration). The expiration notification 51 may also be communicated, for example, to a remote computer 50 or remote device. The mobile wireless communications device 40 may also determine recalled medications 33a-33n, for example, also based upon the lot number or other identifying information.

Figure 11:
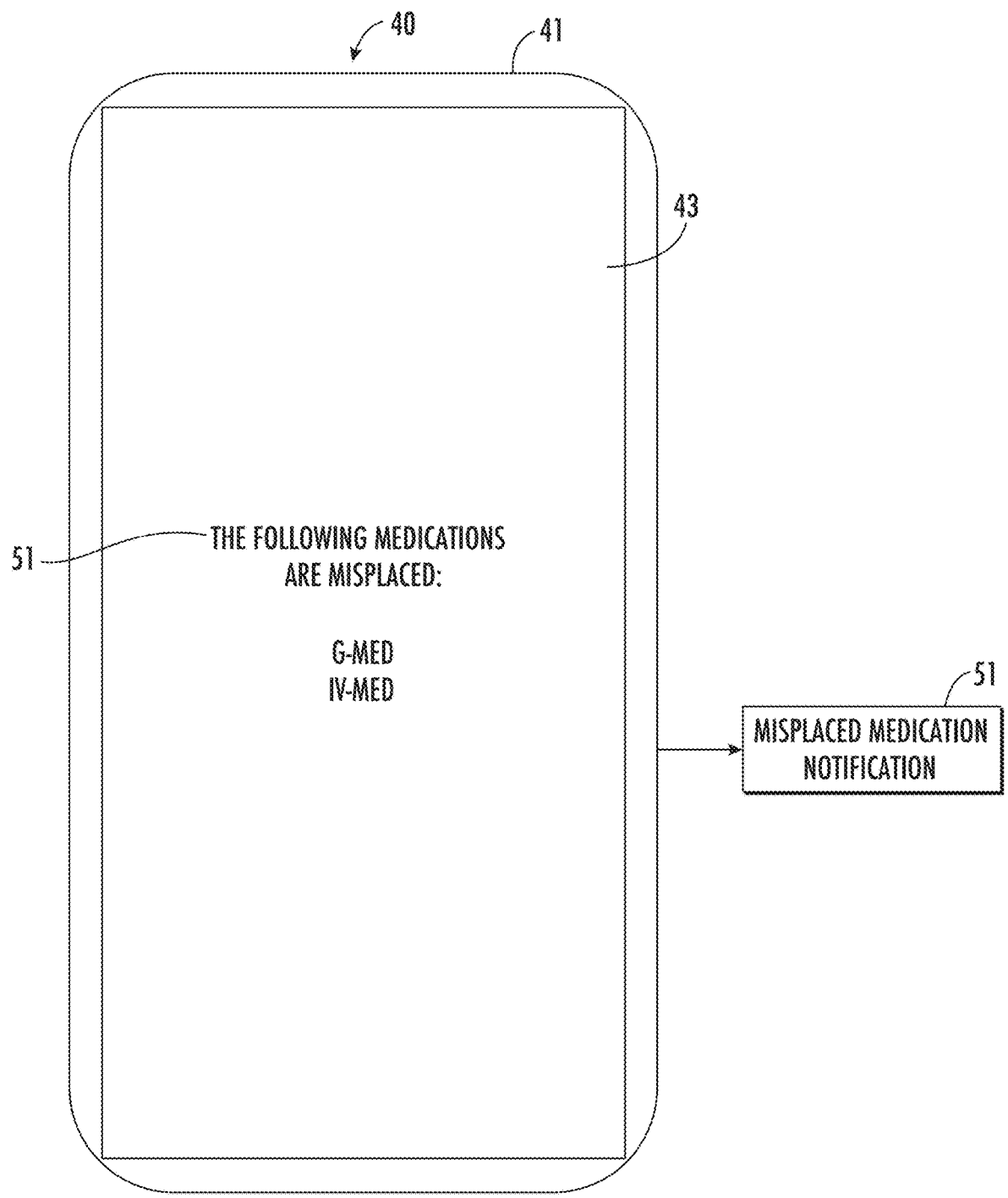
FIG. 11 is a schematic diagram of a mobile wireless communications device in accordance with an embodiment.

Referring now additionally to FIG. 11, the mobile wireless communications device 40 may determine one or more misplaced medications 33a-33n based upon current medication locations and desired medication locations (Block 176). More particularly, the mobile wireless communications device 40 may determine current medication locations within the medication tray 30 from the images 47 (e.g., based upon the medication identifiers 35a-35n) and determine desired medication locations for the tray based upon the tray identifier so that the misplaced medications are determined based upon the current medication locations and the desired medication locations. The mobile wireless communications device 40 may generate a misplaced medication notification 51 for display on the display 43 indicative of a misplaced medication (e.g., not in a correct compartment 32a-32n). The misplaced medication notification 51 may also be communicated, for example, to a remote computer 50 or remote device. In some embodiments, the medication tray 30 may be displayed on the display 43 of the mobile wireless communications device 40 along with the medications and indicia to indicate that one or more medications are misplaced. Operations end at Block 178.

As will be appreciated by those skilled in the art, the medication inventory system 20 may be particularly beneficial for ensuring hospital pharmaceutical trays are refilled efficiently and correctly using any of a variety of handheld device, for example. The medication inventory system 20 may integrate with current pharmacy safety/workflow and tracking technology, and provides pharmacy safety/workflow and tracking technology in a mobile or handheld form factor, thus supporting bring-your-own-device functionality.

Further details of medication trays and related processing of medications therein is described in U.S. Patent Application Publication No. 2019/0333008 to Wolfe et al., and U.S. patent application Ser. Nos. 16/395,343, and 16/395,353, the entire contents of all of which are hereby incorporated by reference.

A method aspect is directed to a method of processing medication inventory in a medication inventory system 20 that includes a medication tray 30 including a plurality of compartments 32a-32n for storing respective medications 33a-33n with each medication having a respective medication identifier 35a-35n associated therewith. The medication tray 30 has a tray identifier 31 associated therewith. The method includes using a mobile wireless communications device 40 to obtain a plurality of images 47 of the medication tray 30 and generate a current medication stocking list 48 of the medication tray from the plurality of images. The method also includes using the mobile wireless communications device 40 to determine the desired medication stocking list 49 for the medication tray 30 based upon the medication tray identifier 31 and determine at least one missing medication 33a-33n based upon the current medication stocking list 48 and the desired medication stocking list.

A computer readable medium aspect is directed to a non-transitory computer readable medium for a medication inventory system 20 that includes a medication tray 30 including a plurality of compartments 32a-32n for storing respective medications 33a-33n with each medication having a respective medication identifier 35a-35n associated therewith. The medication tray 30 has a tray identifier 31 associated therewith, the non-transitory computer readable medium includes computer executable instructions that when executed by a controller 45 of a mobile wireless communications device 40 cause the controller to perform operations. The operations include obtaining a plurality of images 47 of the medication tray 30 and generating a current medication stocking list 48 of the medication tray from the plurality of images. The operations also include determining a desired medication stocking list 49 for the medication tray 30 based upon the tray identifier 31, and determining at least one missing medication 33a-33n based upon the current medication stocking list 48 and the desired medication stocking list.

Figure 12:
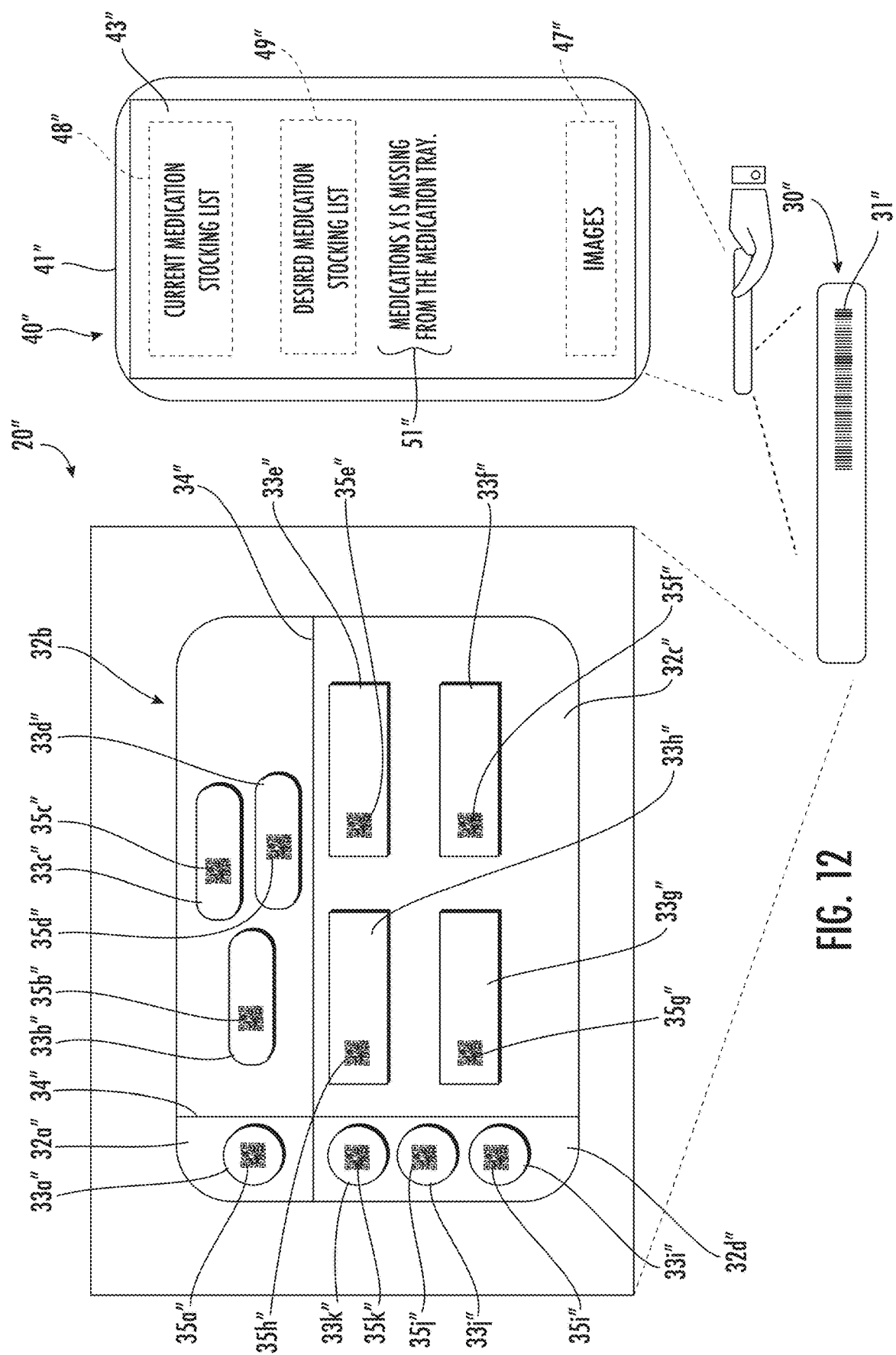
FIG. 12 is a schematic diagram of a medication inventory system in accordance with an embodiment.
Figure 13:
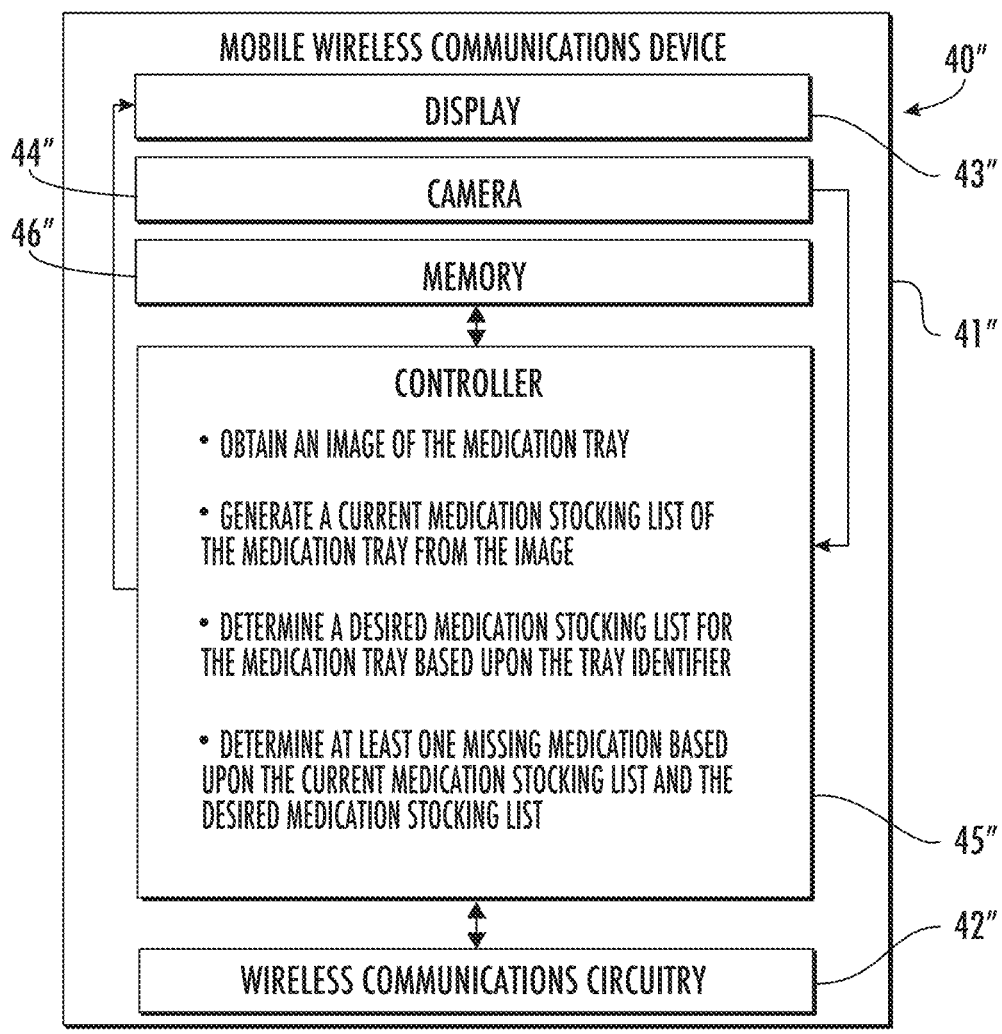
FIG. 13 is a schematic block diagram of the mobile wireless communications device of FIG. 12.

Referring now to FIGS. 12-13, in another embodiment, similar to the embodiments above, a medication inventory system 20" illustratively includes a medication tray 30". The medication tray 30" includes partitions 34" that define compartments 32a"-32n". Each compartment may store a medication 33a"-33n", multiple medications, a medical or medicated device, a medication container that includes individual medications therein, or other item or substance used for medical treatment. Each medication 33a"-33n" has a respective medication identifier 35a"-35n" associated therewith, for example, a barcode, quick-response (QR) code, alphanumeric characters, or other optically recognizable and unique code.

The medication tray 30" has a tray identifier 31" associated therewith. The tray identifier 31" may be in the form of a barcode, for example, that may be printed or applied (e.g., via an adhesive label) on the medication tray 30". The tray identifier 31" may be in the form of another type of identifier, for example, QR code, alphanumeric characters, or other optically recognizable and unique code.

The medication inventory system 20" also includes a mobile wireless communications device 40", illustratively in the form of a smartphone and similar to the embodiments described above. Similarly to the mobile wireless communications device described above, the mobile wireless communications device 40" illustratively includes a housing 41" and wireless communications circuitry 42" carried by the housing. The mobile wireless communications device 40" also includes a display 43", for example, a touch display, carried by the housing 41". A controller 45" is coupled to the wireless communications circuitry 42" and the display 43". A camera 44" is also carried by the housing 41" and coupled to the controller 45". One or more input devices may be carried by the housing 41" and coupled to the controller 45". While the mobile wireless communications device 40" is illustratively in the form of a smartphone, the mobile wireless communications device may be in the form of a tablet, laptop computer, or wearable device, for example.

Figure 14:
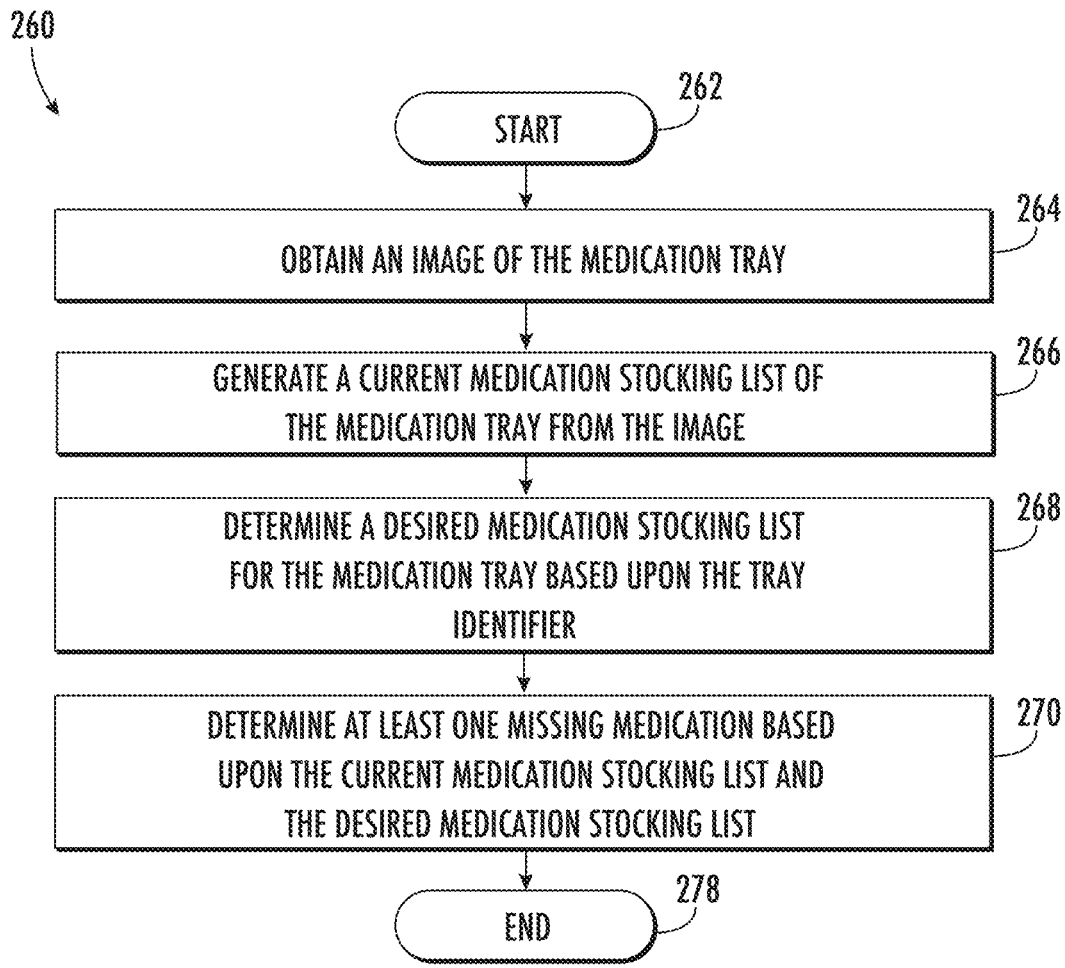
FIG. 14 is a flow diagram illustrating operation of the mobile wireless communications device of FIG. 13.

Referring now additionally to the flowchart 260 in FIG. 14, beginning at Block 262, operations of the mobile wireless communications device 40" of the medication inventory system 20" according to the present embodiments will now be described. At Block 264, the mobile wireless communications device 40" obtains an image 47", for example, a single image, of the medication tray 30". At Block 266, the mobile wireless communications device 40" generates a current medication stocking list 48" of the medication tray 30" from the image 47".

The mobile wireless communications device 40" determines a desired medication stocking list 49" of the medication tray 30" based upon the tray identifier 31" (Block 268). More particularly, the mobile wireless communications device 40" may obtain the desired medication stocking list 49" from a remote computer or database based upon the tray identifier 31". In other words, the tray identifier 31" may be used as an index to retrieve or obtain the desired medication stocking list 49".

The mobile wireless communications device 40", at Block 270, determines one or more missing medications 33e", 33h" based upon the current medication stocking list 48" and the desired medication stocking list 49". More particularly, if a medication 33a"-33n" that is part of the desired medication stocking list 49" is determined to not be in the current medication stocking list 48" (i.e., a medication was not found in the image 47"), a notification 51" may be generated and displayed on the display 43" of the mobile wireless communications device 40". The controller 45" may use image recognition techniques, for example, for identifying the medication identifiers 35a"-35n", to determine missing medications. Operations end at Block 278.

Figure 15:
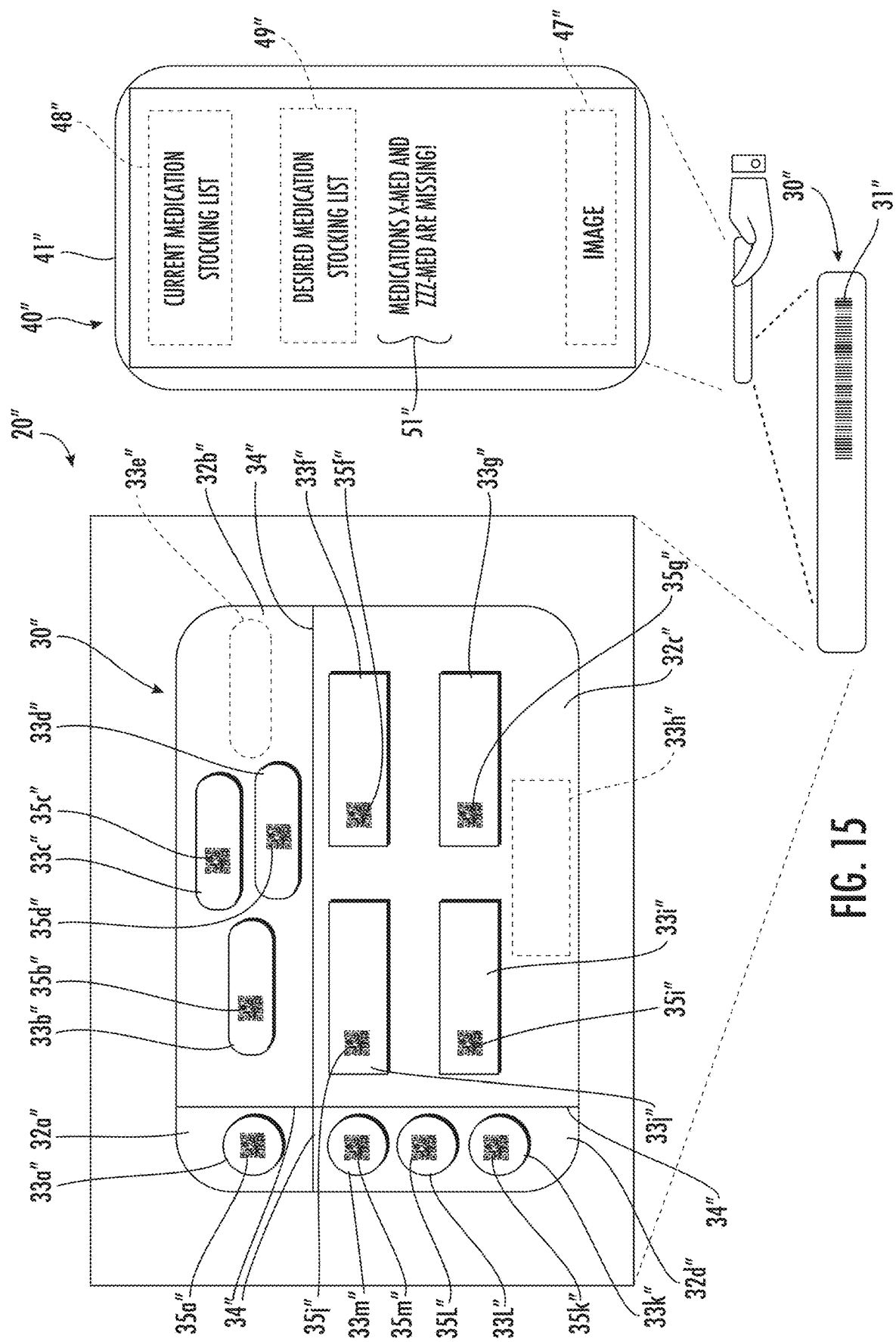
FIG. 15 is a schematic diagram of a medication inventory system in accordance with an embodiment.
Figure 16:
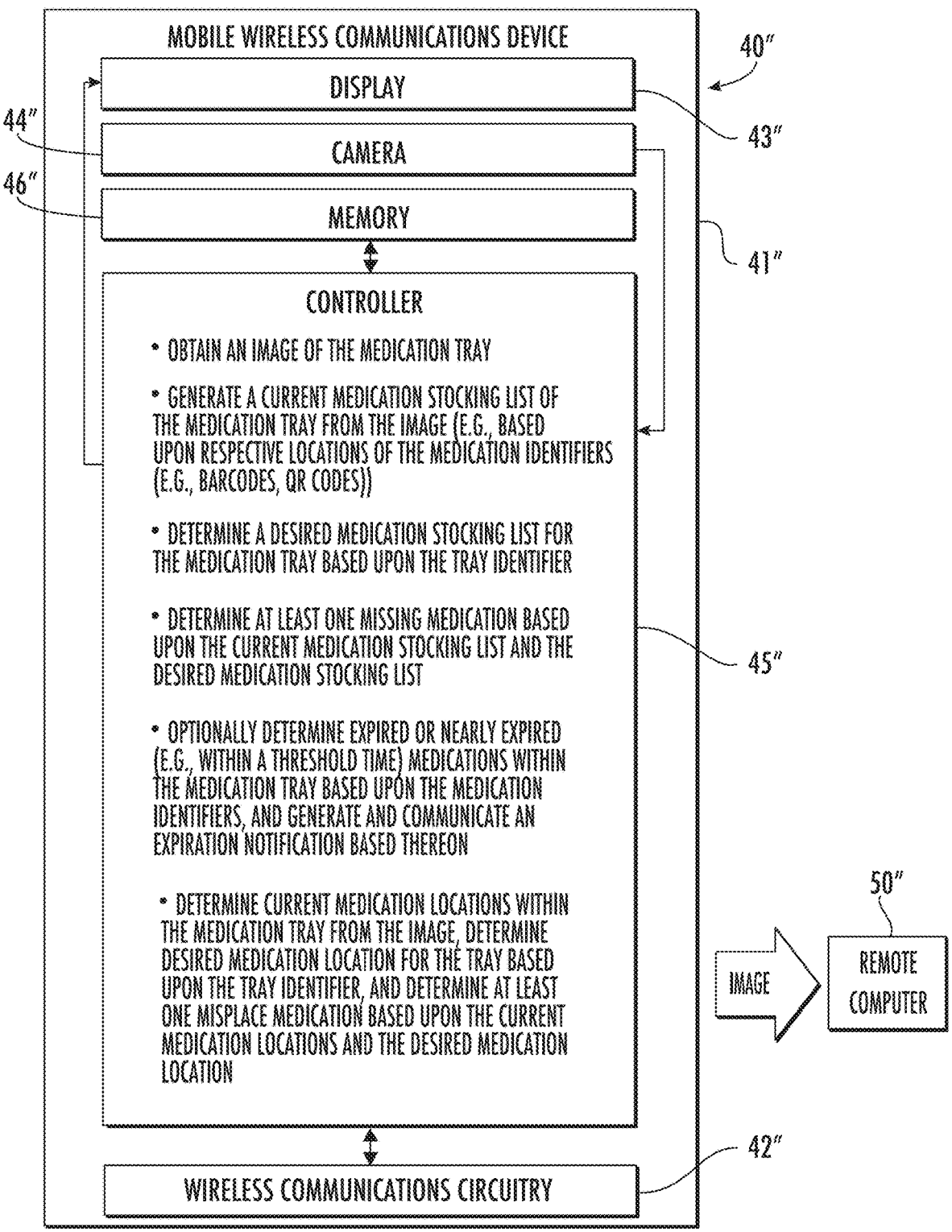
FIG. 16 is a schematic block diagram of a portion of the mobile wireless communications device of FIG. 15 including a remote device.
Figure 17:
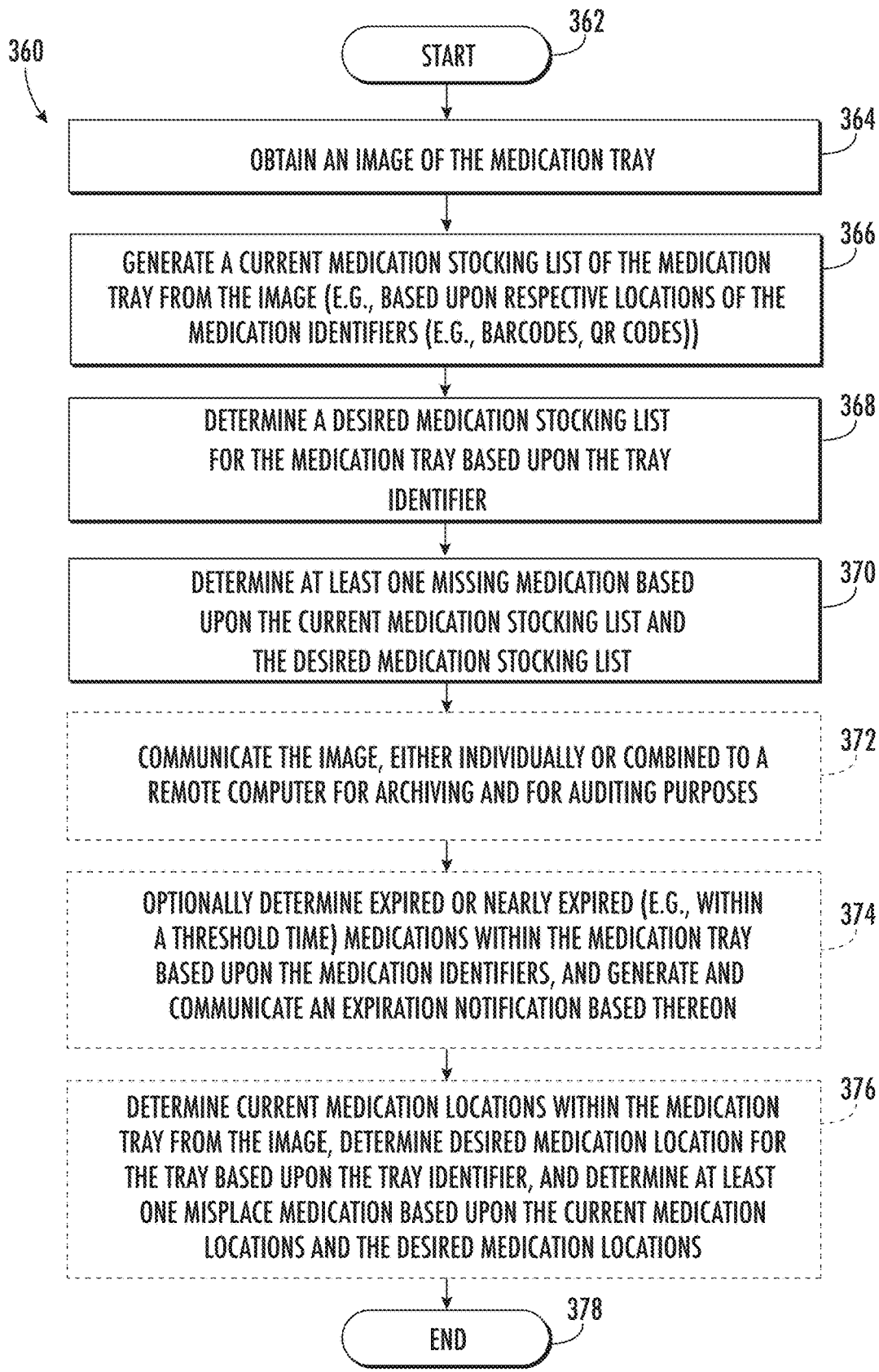
FIG. 17 is a flow diagram illustrating operation of the mobile wireless communications device of FIG. 16.

Referring now to FIGS. 15-16, and the flowchart 360 in FIG. 17, beginning at Block 362 more detailed operations of the mobile wireless communications device 40" with respect to the medication inventory system 20" will now be described. At Block 364, the mobile wireless communications device 40" obtains a single image 47" of the medication tray 30". The image 47" may include, in its field-of-view, the entire medication tray 30". In other words, a given user captures, via the camera 44", an image that includes the entire medication tray 30" or sufficient portion thereof to identify or generate the current medication stocking list 48". For example, edges of the medication tray 30" may be cut-off in the image 47". The image 47" may be obtained from the camera 44" at an orientation that may not be "straight-on", for example. As will be appreciated by those skilled in the art, however, it may be desirable that the single image 47" have a high enough resolution so that both the tray and medication identifiers 31", 35a"-35n" are legible or readable. Thus, it may be desirable to position the mobile wireless communications device 40" including the camera 44" relatively close to the medication tray 30" so that the entire medication tray is included in the image 47" or field of view, but not too far away as to provide a lower resolution of the medications 33a"-33n".

At Block 366, the mobile wireless communications device 40" generates a current medication stocking list 48" of the medication tray 30" from the single image 47". More particularly, the mobile wireless communications device 40" generates the current medication stocking list 48" based upon an image analysis of the image 47". For example, the mobile wireless communications device 40" may generate the current medication stocking list 48" based upon known boundaries, shapes, and other identifiers within the image, which may be based upon respective locations of the medication identifiers 35a"-35n".

The mobile wireless communications device 40" determines a desired medication stocking list 49" of the medication tray 30" based upon the tray identifier 31' (Block 368), for example, using techniques along the lines described above. In some embodiments, desired medication stocking lists 49" for respective medication trays 30" may be stored in the memory 46" of the mobile wireless communications device 40".

The mobile wireless communications device 40", at Block 370, determines one or more missing medications 33e", 33h" (e.g., that may have been used) based upon the current medication stocking list 48" and the desired medication stocking list 49". More particularly, if a medication 33a"-33n" that is part of the desired medication stocking list 49" is determined to not be in the current medication stocking list 48" (i.e., a medication 33e", 33h" was not found in the single image 47"), a notification 51" may be generated and displayed on the display 43" of the mobile wireless communications device 40" and/or communicated. The notification 51" may be in the form of a list, for example, and/or an image of the medication tray with indicia (e.g. color-coded). The controller 45" may use image recognition techniques, for example, for identifying the medication identifiers 35a"-35n", to determine missing medications. In some embodiments, the mobile wireless communications device 40" may determine that a medication 33a"-33n" is missing based upon there being less than a desired number (e.g., a threshold number) of medications in a given compartment 32a"-32n".

In some embodiments, the mobile wireless communications device 40" may wirelessly communicate the single image 47" to a remote computer 50" for archiving and for auditing purposes (Block 372). The missing medications 33e", 33h" may also be wirelessly communicated to the remote computer 50". In some embodiments, the mobile wireless communications device 40" may generate and communicate an invoice for the missing medications 33e", 33h". Alternatively or additionally, the mobile wireless communications device 40" may communicate the missing medications 33e", 33h" to a remote computer 50" for processing, for example, generation and communication of the invoices.

Similar to embodiments described above, the mobile wireless communications device 40" may also determine expired medications 33a"-33n" or nearly expired medications within the medication tray 30" based upon the medication identifiers 35a"-35n" (Block 374), for example, by comparing a lot number of the medication. The mobile wireless communications device 40" may generate an expiration notification 51" for display on the display 43" indicative of an expired medication or nearly expired medication (e.g., within a threshold time period from an actual expiration). The expiration notification 51" may also be communicated, for example, to a remote computer 50" or remote device. The mobile wireless communications device 40" may also determine recalled medications 33a"-33n", for example, also based upon the lot number or other identifying information.

The mobile wireless communications device 40" may also determine one or more misplaced medications 33a'-33n" based upon current medication locations and desired medication locations (Block 376). More particularly, the mobile wireless communications device 40" may determine current medication locations within the medication tray 30" from the single image 47" (e.g., based upon the medication identifiers 35*a*"-35*n*') and determine desired medication locations for the tray based upon the tray identifier 31" so that the misplaced medications are determined based upon the current medication locations and the desired medication locations. The mobile wireless communications device 40" may generate a misplaced medication notification 51" for display on the display 43" indicative of a misplaced medication (e.g., not in a correct compartment 32*a*"-32*n*"). The misplaced medication notification 51" may also be communicated, for example, to a remote computer 50" or remote device. In some embodiments, the medication tray 30" may be displayed on the display 43" of the mobile wireless communications device 40" along with the medications 33*a*"-33*n*" and indicia to indicate that one or more medications are misplaced. Operations end at Block 378.

In some embodiments, the mobile wireless communications device 40" may determine that the single image 47" is not sufficient and may then prompt the user to obtain one or more additional images, for example, of a portion or portions of the medication tray 30" and/or at varying fields of view. More particularly, the mobile wireless communications device 40" may perform a single-image analysis as noted above, and then, if the single-image analysis is insufficient, the mobile wireless communications device may either switch to the multi-image analysis described herein, or supplement the single image with the additional images, for example, by stitching images, overlaying images, or other image processing techniques, so that the overall or combined images are sufficient to generate the current medication list.

A method aspect is directed to a method of processing medication inventory in a medication inventory system 20" that includes a medication tray 30" including a plurality of compartments 32*a*"-32*n*" for storing respective medications 33*a*"-33*n*" with each medication having a respective medication identifier 35*a*"-35*n*" associated therewith. The medication tray 30" has a tray identifier 31" associated therewith. The method includes using a mobile wireless communications device 40" to obtain an image 47" of the medication tray 30", generate a current medication stocking list 48" of the medication tray from the image, and determine a desired medication stocking list 49" for the medication tray based upon the tray identifier 31". The method also includes using the mobile wireless communications device 40" to determine at least one missing medication 33*e*", 33*h*" based upon the current medication stocking list 48" and the desired medication stocking list 49".

A computer readable medium aspect is directed to a non-transitory computer readable medium for a medication inventory system 20" that includes a medication tray 30" including a plurality of compartments 32*a*"-32*n*" for storing respective medications 33*a*"-33*n*" with each medication having a respective medication identifier 35*a*"-35*n*" associated therewith. The medication tray 30" has a tray identifier 31" associated therewith. The non-transitory computer readable medium includes computer executable instructions that when executed by a controller 45" of a mobile wireless communications device 40" cause the controller to perform operations. The operations include obtaining an image 47" of the medication tray 30", generating a current medication stocking list 48" of the medication tray from the image, and determining a desired medication stocking list 49" for the medication tray based upon the tray identifier 31". The operations also include determining at least one missing medication 33*e*", 33*h*" based upon the current medication stocking list 48" and the desired medication stocking list 49".

Figure 18:
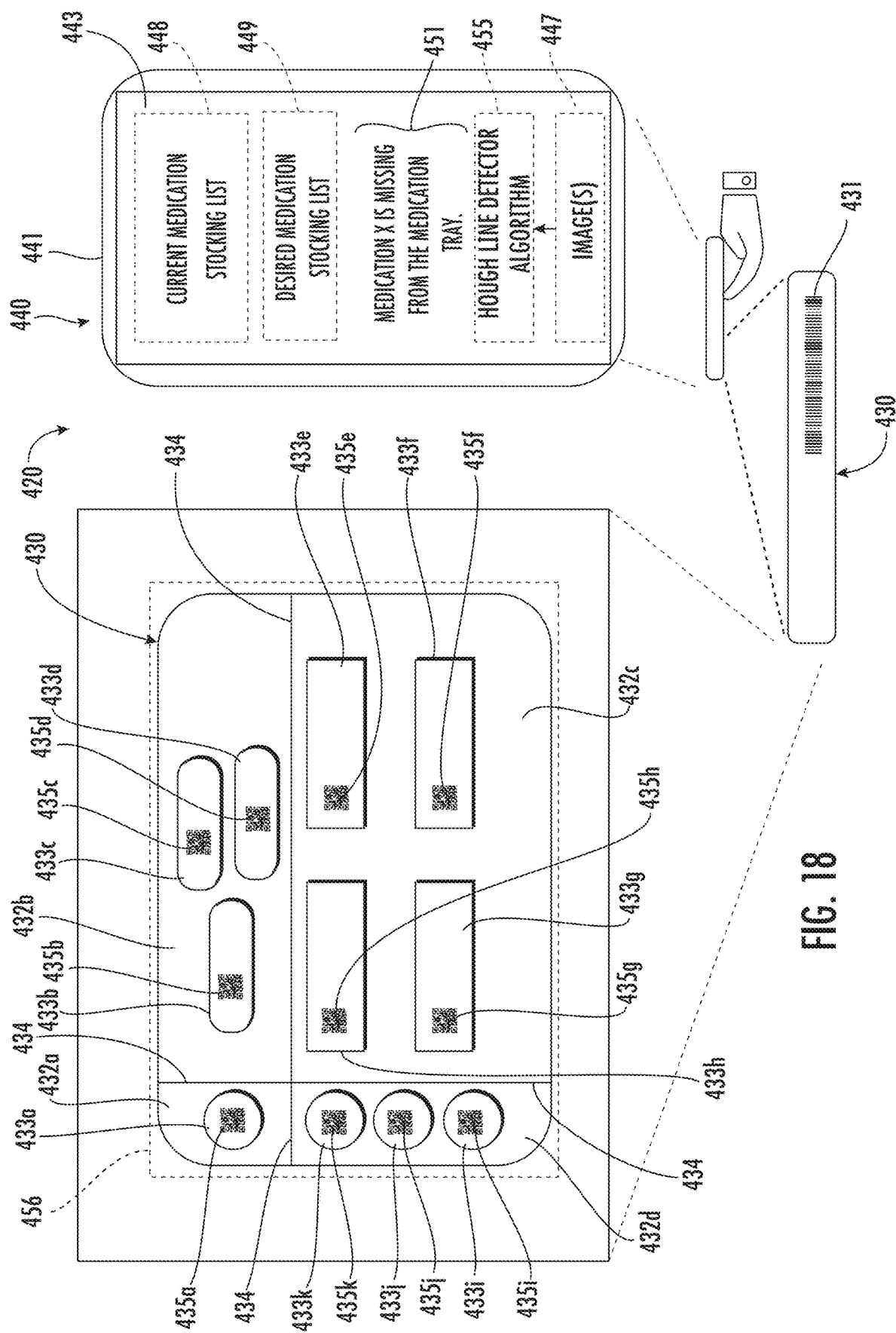
FIG. 18 is a schematic diagram of a medication inventory system in accordance with another embodiment.
Figure 19:
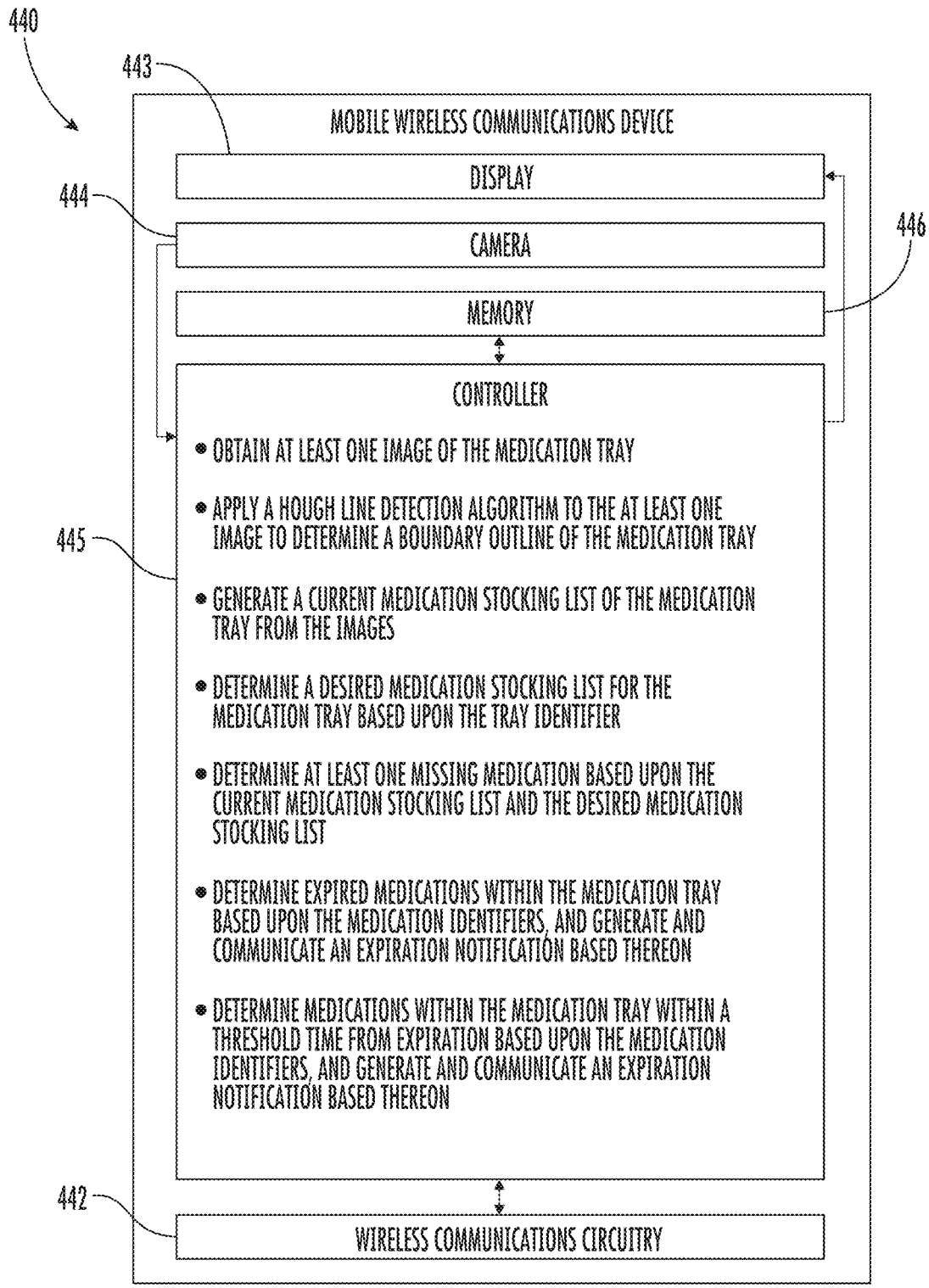
FIG. 19 is a schematic block diagram of the mobile wireless communications device of FIG. 18.

Referring now to FIGS. 18-19, in another embodiment, a medication inventory system 420 includes a medication tray 430 that includes compartments 432*a*-432*n*, defined by partitions 434, for storing respective medications 433*a*-433*n*. Similar to the embodiments described above, each compartment may store a medication 433*a*-433*n*, multiple medications, a medical or medicated device, a medication container that includes individual medications therein, or other item or substance used for medical treatment. For example, the medication tray 430 may be part of a crash cart, as will be appreciated by those skilled in the art. Of course, the medication tray 430 may be used in other medical environments, for example, an examination room, emergency room, treatment room, operating room, etc. For example, the medication tray 430 may be in the form of a drawer within a medication cabinet or medication dispensing cabinet. Each medication 433*a*-433*n* has a respective medication identifier 435*a*-435*n*** associated therewith, for example, a barcode, quick-response (QR) code, alphanumeric characters, or other optically recognizable and unique code.

Also, similarly to the above-described embodiments, the medication tray 430 has a tray identifier 431 associated therewith. The tray identifier 431 may be in the form of a barcode, for example, that may be printed or applied (e.g., via an adhesive label) on the medication tray 430. The tray identifier 431 may be in the form of another type of identifier, for example, QR code, alphanumeric characters, or other optically recognizable and unique code.

The medication inventory system 420 also includes a mobile wireless communications device 440, illustratively in the form of a smartphone. The mobile wireless communications device 440 illustratively includes a housing 441 and wireless communications circuitry 442 carried by the housing. The mobile wireless communications device 440 also includes a display 443, for example, a touch display, carried by the housing 441. A controller 445 is coupled to the wireless communications circuitry 442 and the display 443. A camera 444 is also carried by the housing 441 and coupled to the controller 445. One or more input devices may be carried by the housing 441 and coupled to the controller 445. While the mobile wireless communications device 440 is illustratively in the form of a smartphone, the mobile wireless communications device may be in the form of a tablet, laptop computer, or wearable device, for example.

Figure 20:
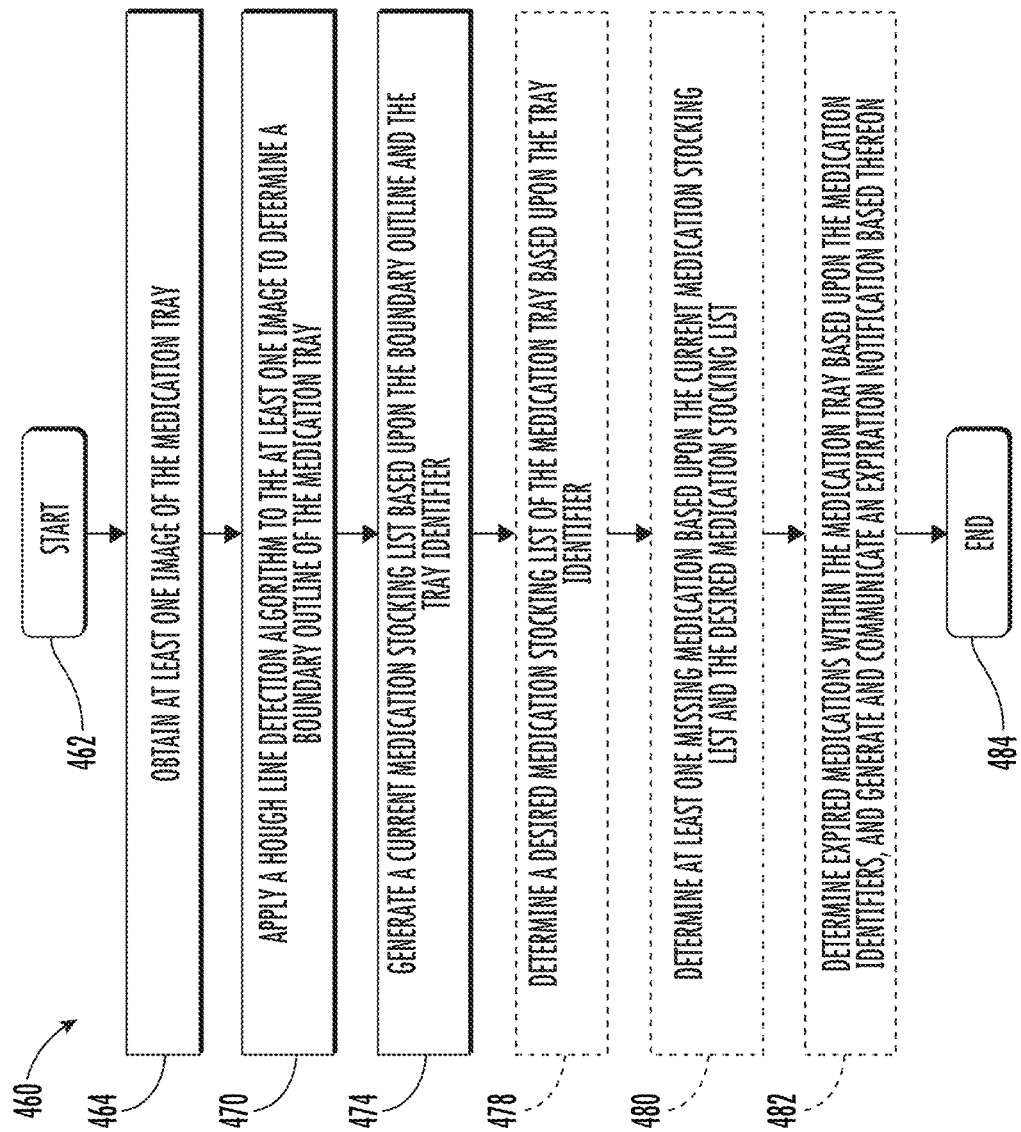
FIG. 20 is a flow diagram illustrating operation of the mobile wireless communications device of FIG. 19.

Referring now additionally to the flowchart 460 in FIG. 20, beginning at Block 462, operations of the mobile wireless communications device 440 of the medication inventory system 420 will now be described. While operations of the mobile wireless communications device 440 are described, it will be appreciated by those skilled in the art that the controller 445 and an associated memory 446 cooperate to perform the operations.

At Block 464, the mobile wireless communications device 440 obtains one or more images 447 of the medication tray 430. At Block 470, the mobile wireless communications device 440 applies a Hough line detection algorithm 455 to the obtained image 447 to determine a boundary outline 456 of the medication tray 430. As will be appreciated by those skilled in the art, the Hough line detection algorithm 455 includes or uses the Hough transform, which is a feature extraction technique used in image analysis, computer vision, and digital image processing and as disclosed in U.S. Pat. No. 3,069,654 to Hough, the entire contents of which are incorporated herein by reference. Application of the Hough line detection algorithm 455 uses a voting procedure to identify imperfect instances of objects within a certain class of shapes, for example, to identify lines in the image.

The mobile wireless communications device 440, at Block 474, generates a current medication stocking list 448 of the medication tray from the image 447 based upon the boundary outline 456 and the tray identifier 431. More particularly, the mobile wireless communications device 440 generates the current medication stocking list 448 similarly to the operations described above, but also generates the current medication stocking list based upon the boundary outline 456. Those skilled in the art will appreciate that by basing the current medication stocking list based upon the boundary outline 456 a more accurate and quicker processing time to generate the current medication stocking list 448 may be obtained since the controller 445 may not process parts of the image outside the boundary outline 456.

The mobile wireless communications device 440 may determine a desired medication stocking list 449 of the medication tray 430 based upon the tray identifier 431 (Block 478), for example, using techniques along the lines described above. In some embodiments, desired medication stocking lists 449 for respective medication trays 430 may be stored in the memory 446 of the mobile wireless communications device 440.

The mobile wireless communications device 440, at Block 480, may determine one or more missing medications (e.g., that may have been used) based upon the current medication stocking list 448 and the desired medication stocking list 449. More particularly, if a medication that is part of the desired medication stocking list 449 is determined to not be in the current medication stocking list 448 (i.e., a medication was not found in the at least one image 447), a notification 451 may be generated and displayed on the display 443 of the mobile wireless communications device 440 and/or communicated. The notification 451 may be in the form of a list, for example, and/or an image of the medication tray with indicia (e.g. color-coded). The controller 445 may use image recognition techniques, for example, for identifying the medication identifiers 435a-435n, to determine missing medications. In some embodiments, the mobile wireless communications device 440 may determine that a medication is missing based upon there being less than a desired number (e.g., a threshold number) of medications in a given compartment.

Figure 21:
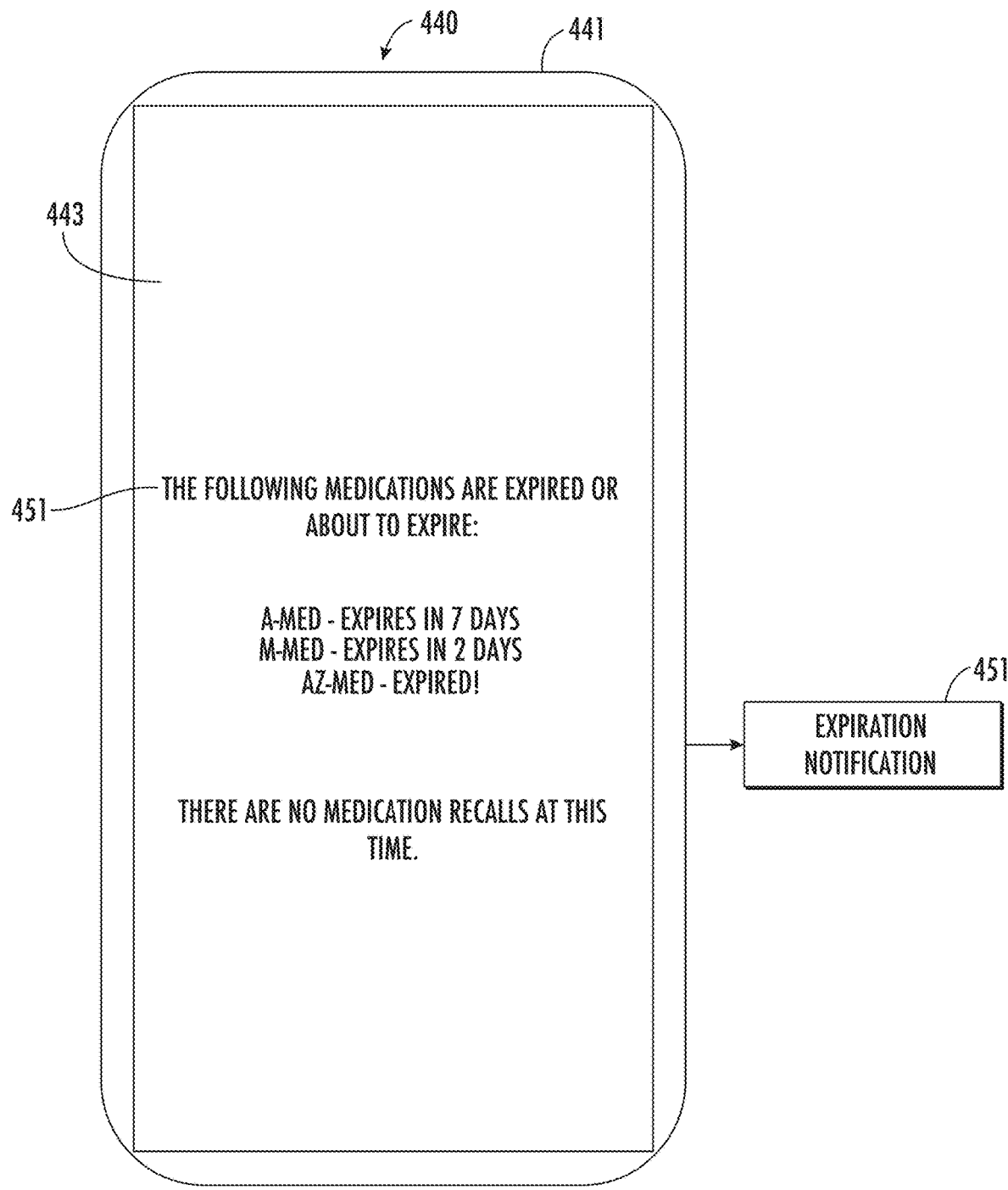
FIG. 21 is a schematic diagram of a mobile wireless communications device in accordance with an embodiment.

Referring now additionally to FIG. 21, the mobile wireless communications device 440 may also determine expired medications or nearly expired medications within the medication tray 430 based upon the medication identifiers 435a-435n (Block 482), for example, by comparing a lot number of the medication. The mobile wireless communications device 440 may generate an expiration notification 451 for display on the display 443 indicative of an expired medication or nearly expired medication (e.g., within a threshold time period from an actual expiration). The expiration notification 451 may also be communicated, for example, to a remote computer 450 or remote device. The mobile wireless communications device 440 may also determine recalled medications, for example, also based upon the lot number or other identifying information. Operations end at Block 484.

Figure 22:
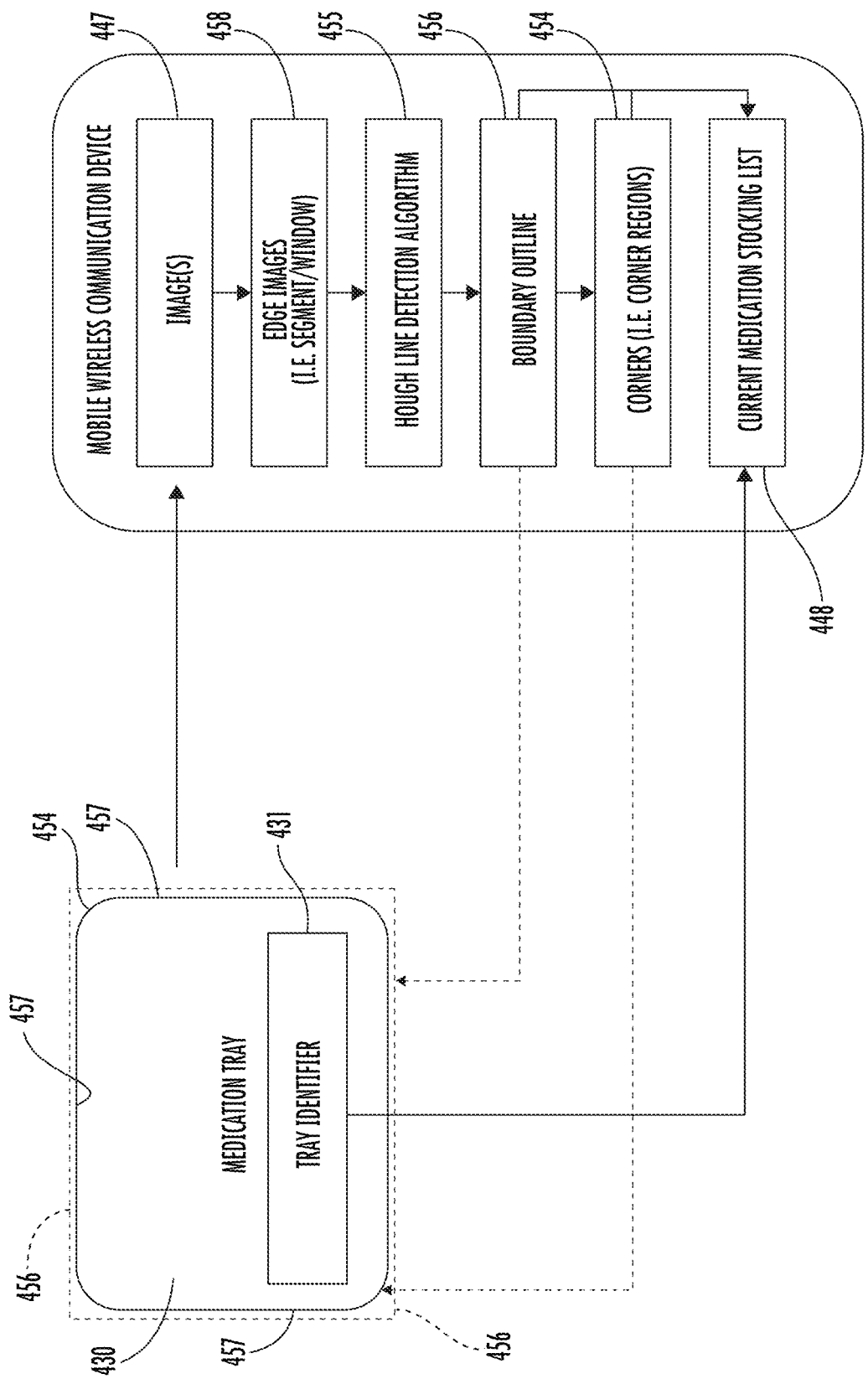
FIG. 22 is a schematic diagram of a medication inventory system in accordance with an embodiment.
Figure 23:
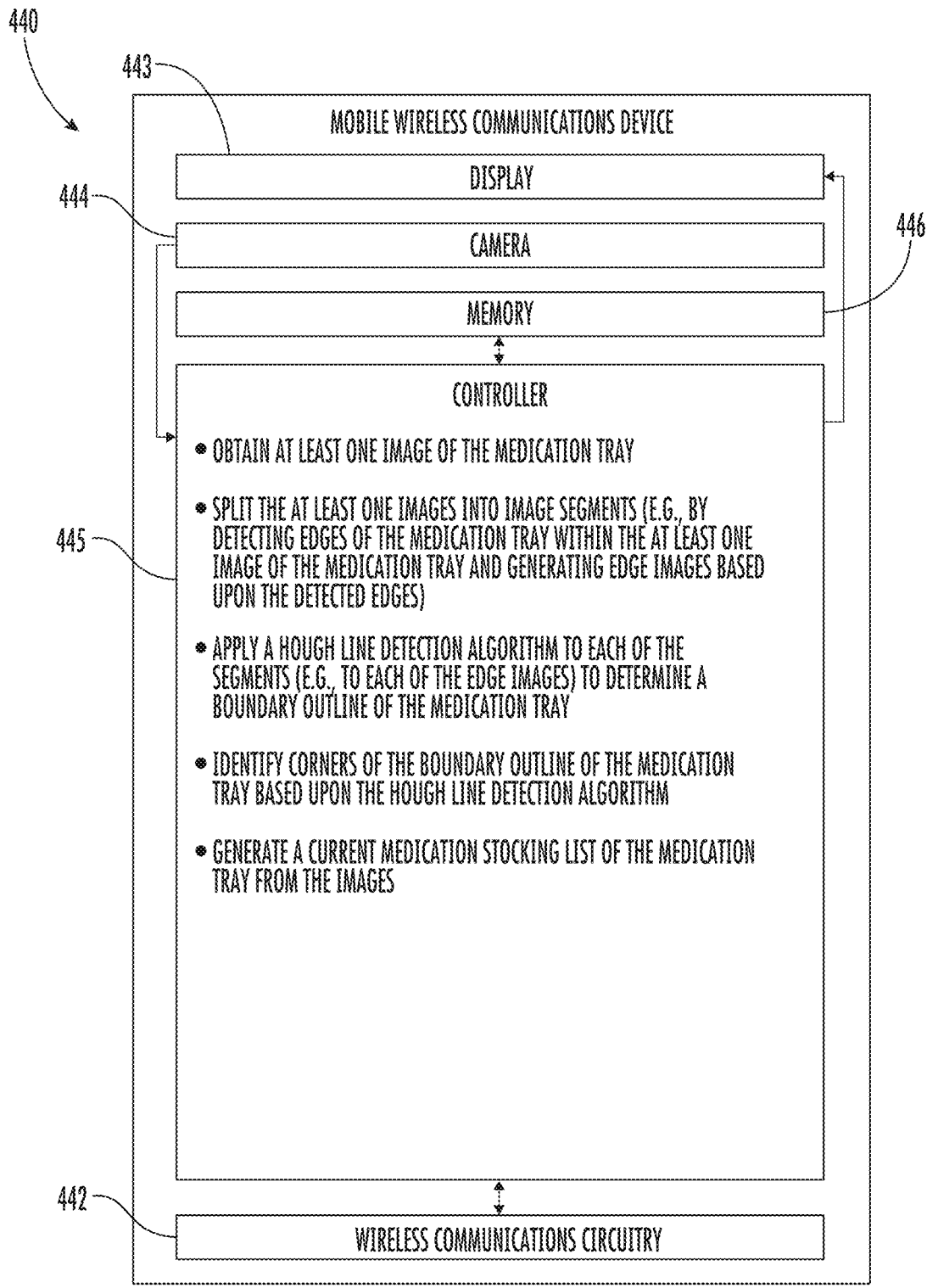
FIG. 23 is a schematic block diagram of the mobile wireless communications device of FIG. 22.
Figure 24:
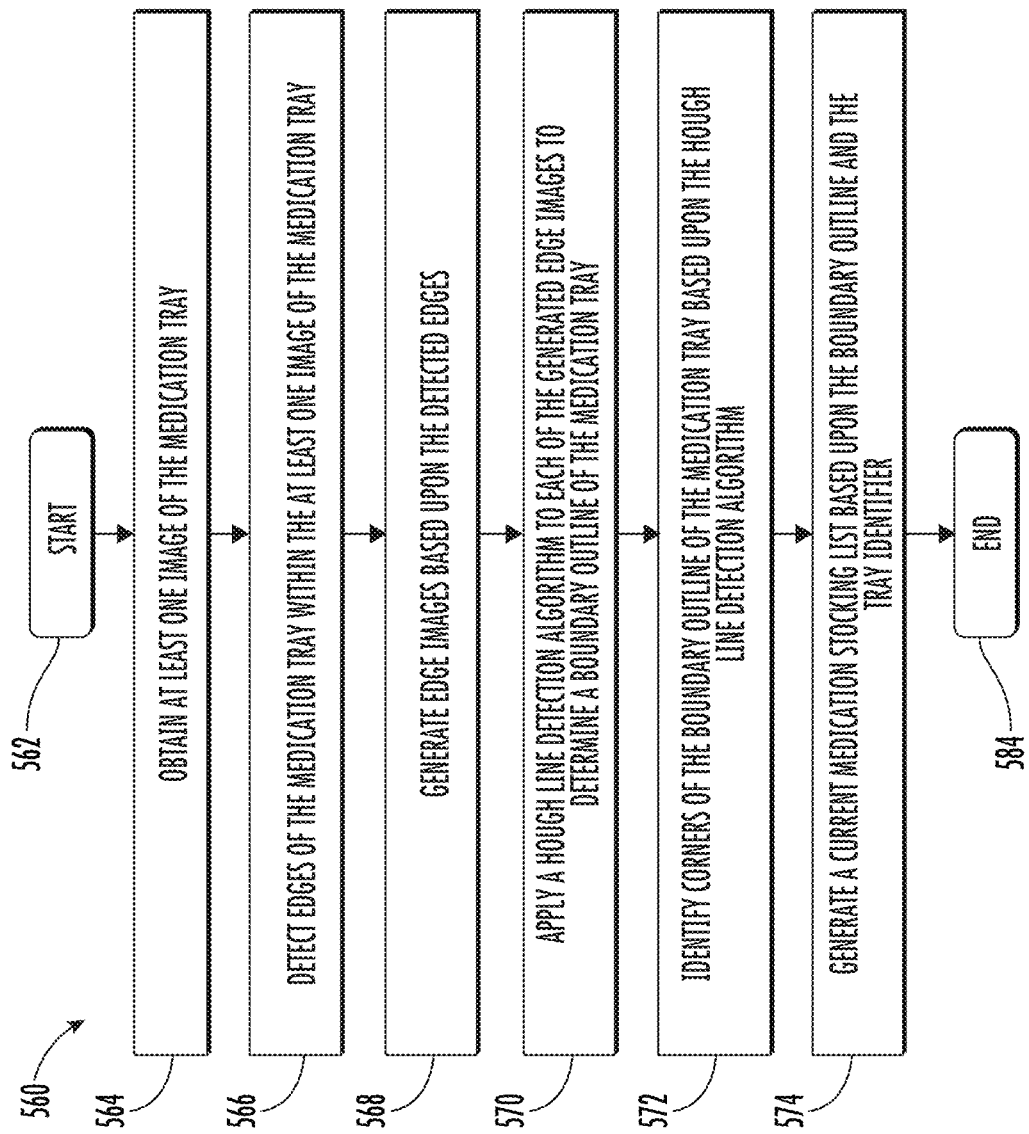
FIG. 24 is a flow diagram illustrating operation of the mobile wireless communications device of FIG. 23.

Referring now to FIGS. 22-23 and the flowchart 560 in FIG. 24, beginning at Block 562 more detailed operations of the mobile wireless communications device 440 with respect to the medication inventory system 420 will now be described. At Block 564, the mobile wireless communications device 440 obtains at least one image 447 of the medication tray 430.

The mobile wireless communications device 440 splits the at least one image 447 into image segments for applying the Hough line detection algorithm 455. More particularly, the mobile wireless communications device 440 detects edges 457 of the medication tray 430 within the images (Block 566). These edges 457 may be considered initial edges and be detected using image recognition techniques, for example, by determining pixel boundaries within the images 447. The mobile wireless communications device 440 generates edge images 458 based upon the detected edges 457 (Block 568), which may be conceptually be considered segments or windows and may be relatively small compared to the overall image 447. The segments or windows 458, may have a square shape, for example, 32×32 pixels. Of course, each window or segment 458 may have another size.

At Block 570, the mobile wireless communications device 440 applies the Hough line detection algorithm 455 to each of the generated edge images 458 or segments. More particularly, the application of the Hough line detection algorithm 455 identifies a major Hough line feature within each window 458, for example, a single major Hough line feature by voting.

At Block 572, the mobile wireless communications device 440 identifies and tracks corners 454 of each window 458 defining a corner region based upon the Hough line detection algorithm 455. More particularly, based upon the major Hough line features, the tray identifier 431, for example, and assumptions of the pose or orientation of the camera 444 or mobile wireless communications device 440 the inner and outer extents of each corner region 454 are generated and thus four candidate corner regions are tracked. Those skilled in the art will appreciate that relative orientation may be determined based upon the mobile wireless communications device, for example, accelerometers, and/or based upon image analysis.

Figure 25:
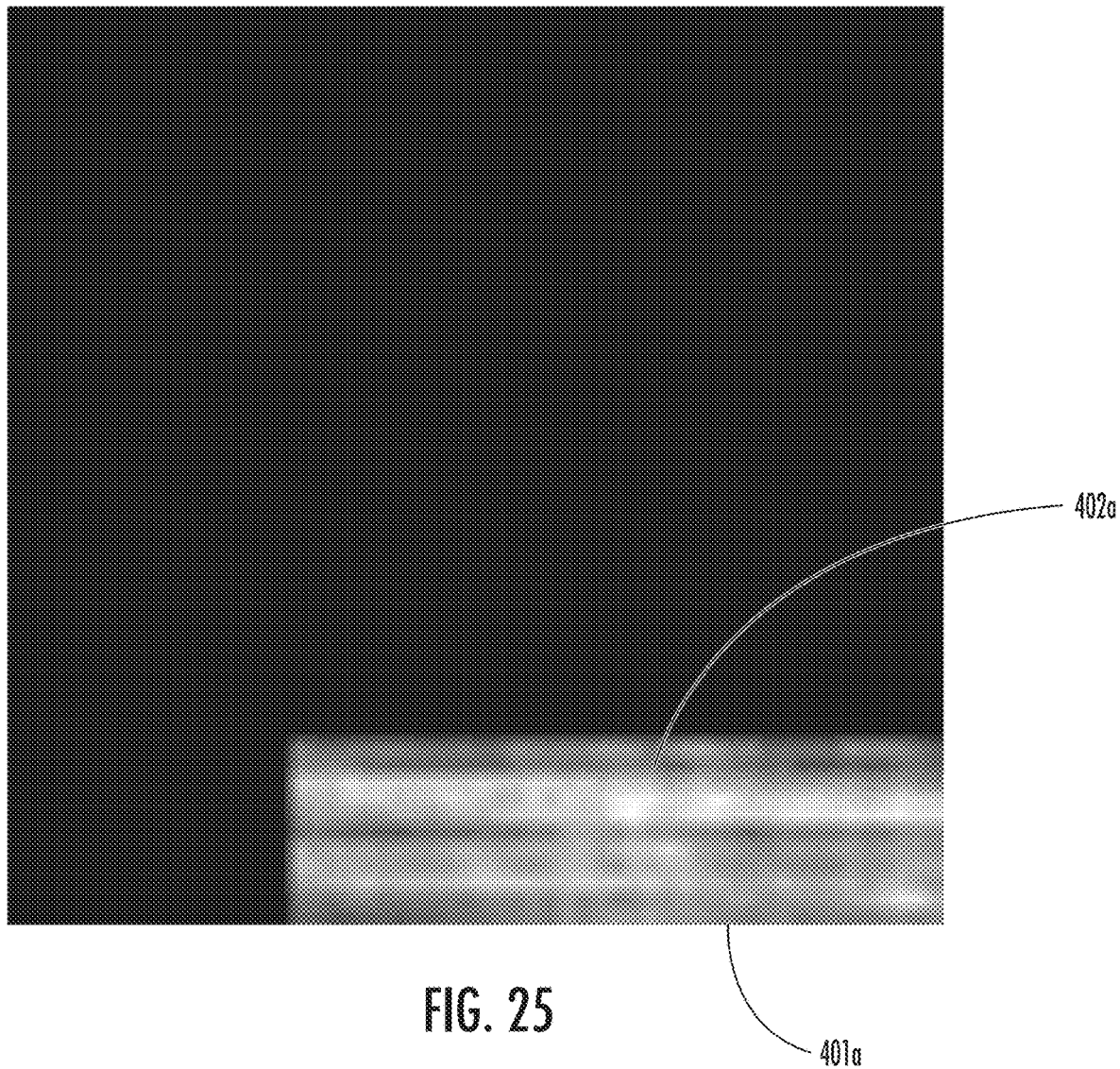
FIG. 25 is an exemplary image identifying a boundary outline of a medication tray in accordance with an embodiment.
Figure 26:
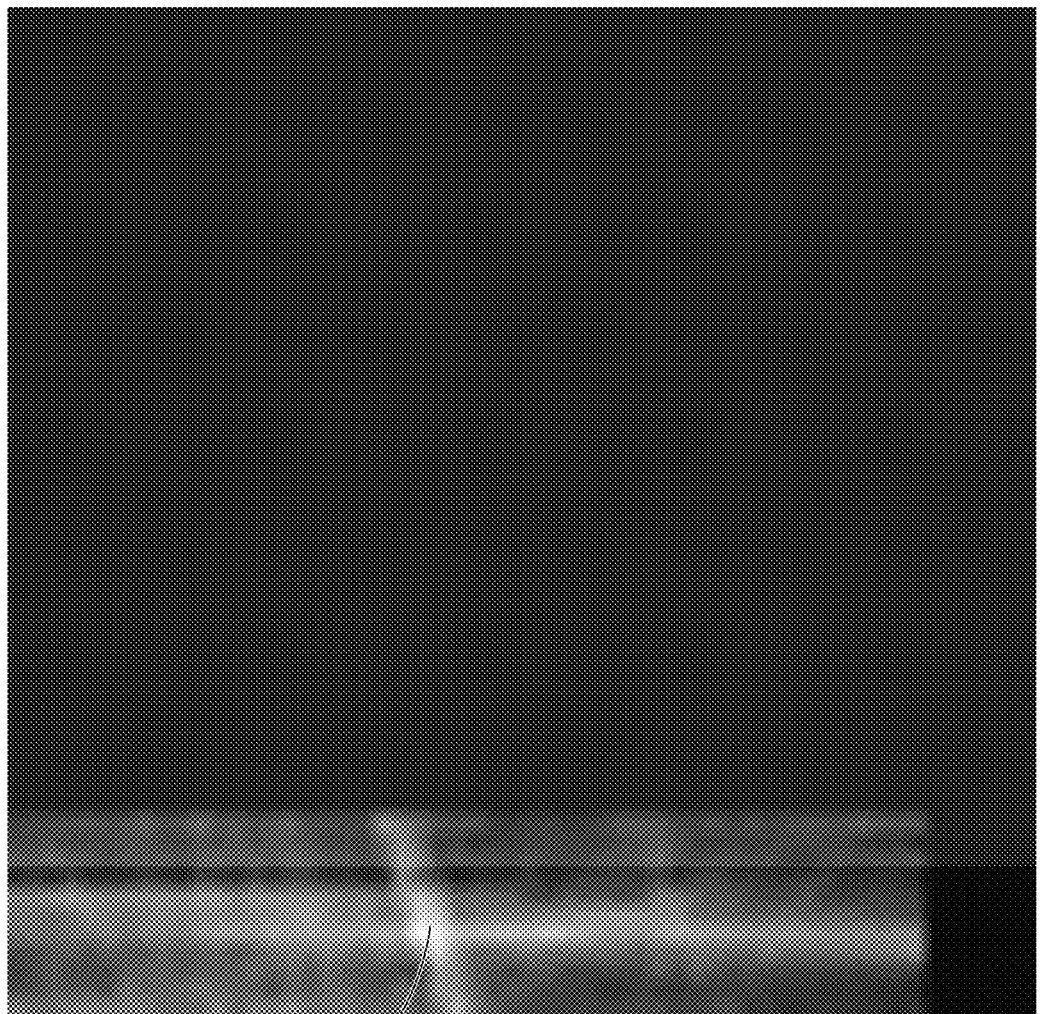
FIG. 26 is another exemplary image identifying a boundary outline of a medication tray in accordance with an embodiment.
Figure 27:
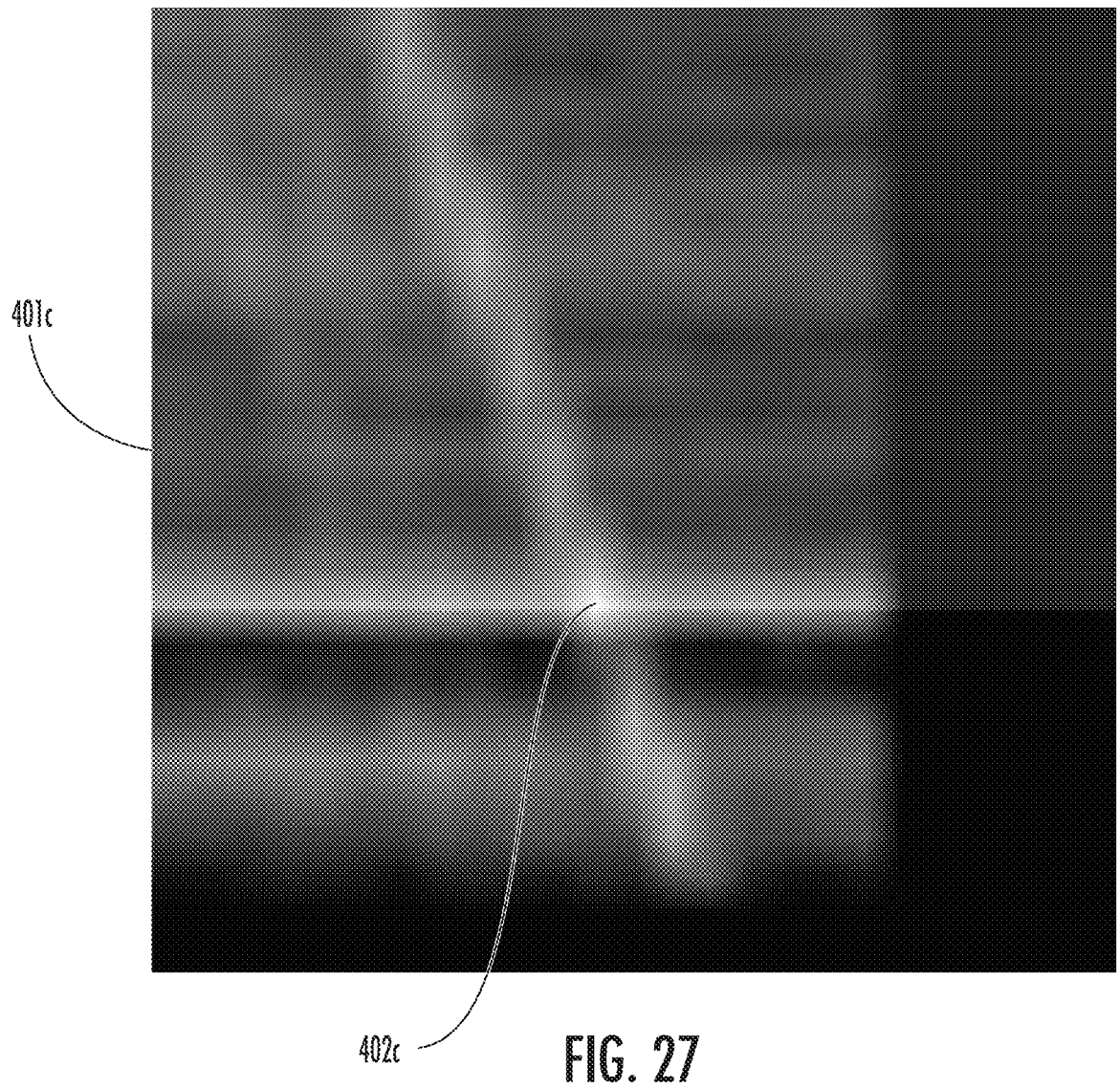
FIG. 27 is another exemplary image identifying a boundary outline of a medication tray in accordance with an embodiment.
Figure 28:
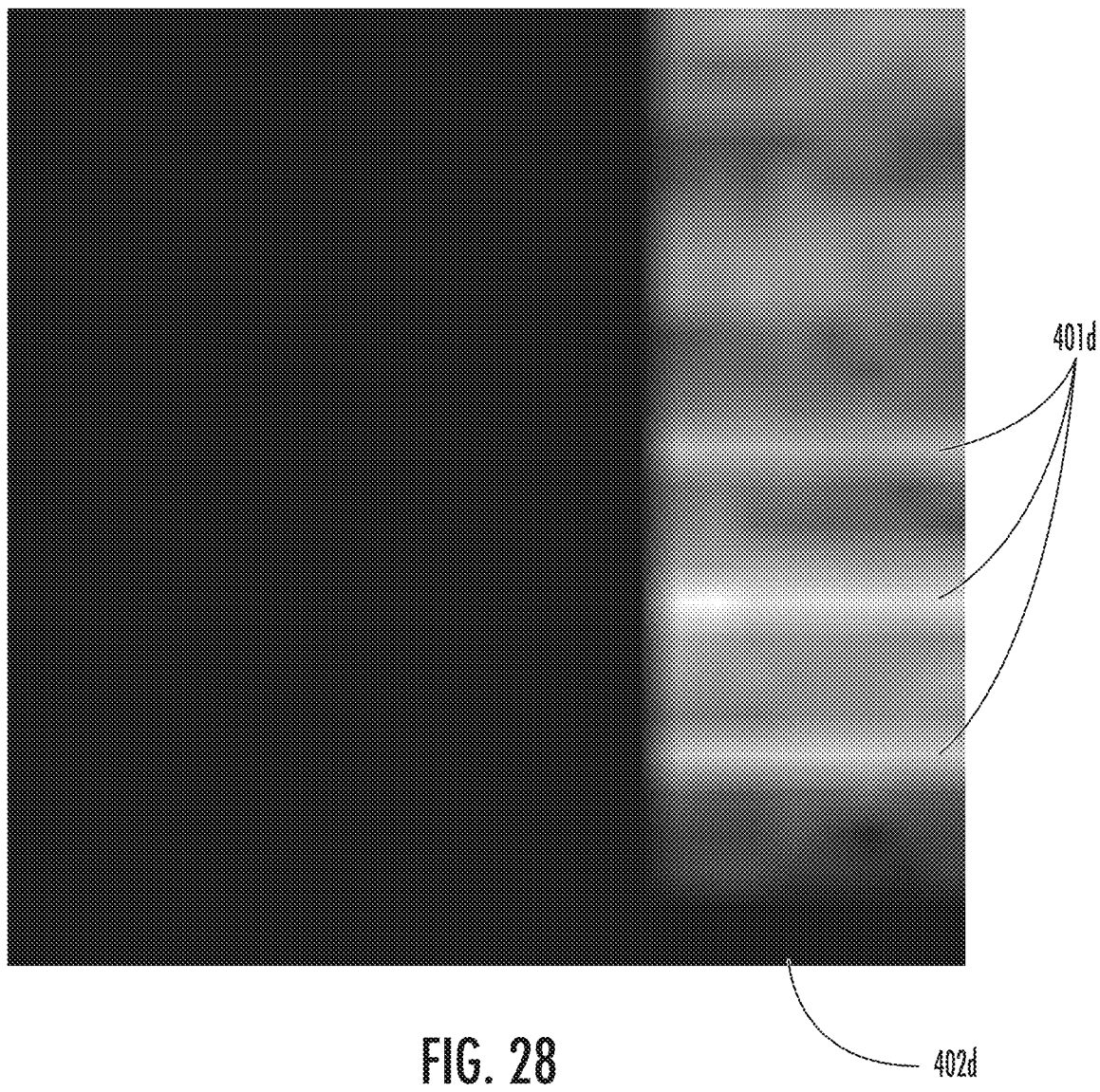
FIG. 28 is another exemplary image identifying a boundary outline of a medication tray in accordance with an embodiment.

After each segment 458 has individually voted for the major Hough line feature within the segment, those lines are extended into the four candidate corner regions 454 one by one. Within each candidate corner region 454, a new temporary image is created and each segment 458 votes for the line extended into that region 454. This may be achieved by adding "1" to each pixel that lies on the line extended into the region. Once complete, in each corner region 454, the brightest pixel is returned as the corner's location. Referring briefly to the images in FIGS. 19-22, exemplary lines that extended into the corner 454 are illustrated 401a (FIG. 25), 401b (FIG. 26), 401c (FIG. 27), 401d (FIG. 28), along with the brightest pixel 402a (FIG. 25), 402b (FIG. 26), 402c (FIG. 27), 402d (FIG. 28). Those skilled in the art will appreciate that the brightest pixel is probabilistically the actual corner is within one segment 458 of that location. A current medication stocking list 448 is generated based upon the boundary outline 456 and the tray identifier 431 (Block 574). Operations end at Block 584.

While operations have been described with respect to one image, the mobile wireless communications device 440 may obtain more than one image 447, which may be at different fields of view relative to the medication tray 430. In the case where multiple images 447 are obtained, the mobile wireless communications device 440 may determine the boundary outline 456 based upon the different fields of view relative to the medication tray 430, for example, using techniques described above with respect to the embodiments illustrated in FIGS. 4-7. Moreover, the mobile wireless communications device 440 may apply the Hough line detection algorithm 455 and operations described above to each image and aggregate, combine, average, or interpolate the determined boundary outlines to determine a final boundary outline 456.

As will be appreciated by those skilled in the art, the medication inventory system 440 advantageously detects the boundary outline 456 or extent of the medication tray in different operations condition. This is in contrast to approaches where operations are dependent on the image obtained being aligned and held, for example, by a user directly above a center of a medication tray. The medication inventory system 440 also may decrease processing times by not having to process portions of an image or images outside of the boundary outline 456.

Additionally, the segmentation and/or inclusion of identification of corners, as described herein may be particularly helpful for addressing the non-linear nature of camera lenses, existing long vertical and horizontal features both in the medication tray itself as well as the surrounding environment, and imprecise edge detection, for example. Moreover, the medication inventory system 420 addresses shortcoming in other approaches, such as, for example, contour tracing, which detects edge with imprecision (pixels that are part of the edge not being detected), and contours both external and internal to the medication tray 430 are detected as part of the tray edge or the boundary outline 456 of the medication tray.

Indeed, the medication inventory system 420 described herein may provide a robust technique to address a variety of distortions and imperfections as well as occlusion of the boundary outline 456 of the medication tray 430. Moreover, the segmentation may permit the algorithm to disregard relatively small errors within each segment, and the corner voting process may permit the algorithm to disregard errors affecting entire segments, as long as the majority of segments are correct, for example. The relatively large segment size also allows for vote combining, where slightly imprecise edge detection may permit two segments to vote for the same segment, instead of disparate pixels within the segment.

A method aspect is directed to a method of processing medication inventory in a medication inventory system 420 that includes a medication tray 430 including a plurality of compartments 432a-432n for storing respective medications 433a-433n. The medication tray 430 may have a tray identifier 431 associated therewith. The method includes using a mobile wireless communications 440 device to obtain at least one image 447 of the medication tray 430, and apply a Hough line detection algorithm 455 to the at least one image to determine a boundary outline 456 of the medication tray. The method also includes using the mobile wireless communications device 440 to generate a current medication stocking list 448 of the medication tray 430 based upon the boundary outline 456 and the tray identifier 431 from the at least one image 447.

A computer readable medium aspect is directed to a non-transitory computer readable medium for a medication inventory system 420 that includes a medication tray 430 including a plurality of compartments 432a-432n for storing respective medications 433a-433n, the medication tray having a tray identifier 431 associated therewith. The non-transitory computer readable medium includes computer executable instructions that when executed by a controller 445 of a mobile wireless communications device 440 cause the controller to perform operations. The operations include obtaining at least one image 447 of the medication tray 430, and applying a Hough line detection algorithm 455 to the at least one image to determine a boundary outline 456 of the medication tray. The operations also include generating a current medication stocking 448 list of the medication tray 430 based upon the boundary outline 456 and the tray identifier 431 from the at least one image.

While several embodiments have been described herein, it should be appreciated by those skilled in the art that any element or elements from one or more embodiments may be used with any other element or elements from any other embodiment or embodiments. Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A medication inventory system comprising:
   a medication tray comprising a plurality of partitions defining a plurality of compartments for storing respective medications, the medication tray having a tray identifier associated therewith; and
   a mobile wireless communications device configured to
      obtain at least one image of the medication tray,
      detect edges of the medication tray and generate a plurality of edge images based upon the detected edges,
      apply a Hough line detection algorithm to the plurality of edge images to determine a boundary outline of the medication tray,
      identify corners of the boundary outline of the medication tray based upon the Hough line detection algorithm, and
      generate a current medication stocking list of the medication tray based upon the boundary outline, the identified corners, respective locations of the medications within the medication tray, and the tray identifier from the at least one image.

2. The medication inventory system of claim 1 wherein the mobile wireless communications device is configured to obtain a plurality of images of the medication tray and apply the Hough line detection algorithm to the plurality of images to determine the boundary outline of the medication tray.

3. The medication inventory system of claim 2 wherein the plurality of images of the medication tray comprises a plurality of images of the medication tray having different fields of view relative to the medication tray; and wherein the mobile wireless communications device is configured to determine the boundary outline of the medication tray based upon the different fields of view.

4. The medication inventory system of claim 1 wherein the mobile wireless communications device is configured to determine a desired medication stocking list for the medication tray based upon the tray identifier.

5. The medication inventory system of claim 4 wherein the mobile wireless communications device is configured to determine at least one missing medication based upon the current medication stocking list and the desired medication stocking list.

6. The medication inventory system of claim 1 wherein each medication has a respective medication identifier associated therewith; and wherein the mobile wireless communications device is configured to determine expired medications within the medication tray based upon the medication identifiers, and generate and communicate an expiration notification based thereon.

7. The medication inventory system of claim 1 wherein the mobile wireless communications device is configured to determine medications within the medication tray within a threshold time from expiration based upon the medication identifiers, and generate and communicate an expiration notification based thereon.

8. A mobile wireless communications device for a medication inventory system comprising a medication tray comprising a plurality of partitions defining a plurality of compartments for storing respective medications, the medication tray having a tray identifier associated therewith, the mobile wireless communications device comprising:
a controller and an associated memory configured to
obtain at least one image of the medication tray,
detect edges of the medication tray and generate a plurality of edge images based upon the detected edges,
apply a Hough line detection algorithm to the plurality of edge images to determine a boundary outline of the medication tray,
identify corners of the boundary outline of the medication tray based upon the Hough line detection algorithm, and
generate a current medication stocking list of the medication tray based upon the boundary outline, the identified corners, respective locations of the medications within the medication tray, and the tray identifier from the at least one image.

9. The mobile wireless communications device of claim 8 wherein the controller is configured to obtain a plurality of images of the medication tray and apply the Hough line detection algorithm to the plurality of images to determine the boundary outline of the medication tray.

10. A method of processing medication inventory in a medication inventory system comprising a medication tray comprising a plurality of partitions defining a plurality of compartments for storing respective medications, the medication tray having a tray identifier associated therewith, the method comprising:
using a mobile wireless communications device to
obtain at least one image of the medication tray,
detect edges of the medication tray and generate a plurality of edge images based upon the detected edges,
apply a Hough line detection algorithm to the plurality of edge images to determine a boundary outline of the medication tray,
identify corners of the boundary outline of the medication tray based upon the Hough line detection algorithm, and
generate a current medication stocking list of the medication tray based upon the boundary outline, the identified corners, respective locations of the medications within the medication tray, and the tray identifier from the at least one image.

11. The method of claim 10 wherein using the mobile wireless communications device comprises using the mobile wireless communications device to obtain a plurality of images of the medication tray and apply the Hough line detection algorithm to the plurality of images to determine the boundary outline of the medication tray.

12. A non-transitory computer readable medium for a medication inventory system comprising a medication tray comprising a plurality of partitions defining a plurality of compartments for storing respective medications, the medication tray having a tray identifier associated therewith, the non-transitory computer readable medium comprising computer executable instructions that when executed by a controller of a mobile wireless communications device cause the controller to perform operations comprising:
obtaining at least one image of the medication tray;
detecting edges of the medication tray and generating a plurality of edge images based upon the detected edges;
applying a Hough line detection algorithm to the plurality of edge images to determine a boundary outline of the medication tray;
identifying corners of the boundary outline of the medication tray based upon the Hough line detection algorithm; and
generating a current medication stocking list of the medication tray based upon the boundary outline, the identified corners, respective locations of the medications within the medication tray, and the tray identifier from the at least one image.

13. The non-transitory computer readable medium of claim 12 wherein the operations comprise obtaining a plurality of images of the medication tray and applying the Hough line detection algorithm to the plurality of images to determine the boundary outline of the medication tray.

14. The medication inventory system of claim 1 wherein the mobile wireless communications device is configured to apply the Hough line detection algorithm to identify a major Hough line feature within each of the plurality of edge images, and identify the corners of the boundary outline of the medication tray based upon the major Hough line feature.

15. The medication inventory system of claim 14 wherein the mobile wireless communications device is configured to generate a temporary image within ones of the plurality of edge images corresponding to identified corners, and within each temporary image adjusting each pixel associated with the major Hough line feature to identify the corners.

16. The medication inventory system of claim 1 wherein the mobile wireless communications device is configured to generate the current medication stocking list based upon an orientation of the mobile wireless communications device.

17. The mobile wireless communications device of claim 8 wherein the controller is configured to apply the Hough line detection algorithm to identify a major Hough line feature within each of the plurality of edge images, and identify the corners of the boundary outline of the medication tray based upon the major Hough line feature.

18. The mobile wireless communications device of claim 17 wherein the controller is configured to generate a temporary image within ones of the plurality of edge images corresponding to identified corners, and within each temporary image adjusting each pixel associated with the major Hough line feature to identify the corners.

19. The mobile wireless communications device of claim 8 wherein the controller is configured to generate the current medication stocking list based upon an orientation of the mobile wireless communications device.

20. The method of claim 10 wherein using the mobile wireless communications device comprises using the mobile wireless communications device to apply the Hough line detection algorithm to identify a major Hough line feature within each of the plurality of edge images, and identify the corners of the boundary outline of the medication tray based upon the major Hough line feature.

21. The method of claim 20 wherein using the mobile wireless communications device comprises using the mobile wireless communications device to generate a temporary image within ones of the plurality of edge images corresponding to identified corners, and within each temporary image adjusting each pixel associated with the major Hough line feature to identify the corners.

22. The method of claim 10 wherein using the mobile wireless communications device comprises using the mobile wireless communications device to generate the current medication stocking list based upon an orientation of the mobile wireless communications device.

23. The non-transitory computer readable medium of claim 12 wherein the operations comprise applying the Hough line detection algorithm to identify a major Hough line feature within each of the plurality of edge images, and identifying the corners of the boundary outline of the medication tray based upon the major Hough line feature.

24. The non-transitory computer readable medium of claim 23 wherein the operations comprise generating a temporary image within ones of the plurality of edge images corresponding to identified corners, and within each temporary image adjusting each pixel associated with the major Hough line feature to identify the corners.

25. The non-transitory computer readable medium of claim 12 wherein the operations comprise generating the current medication stocking list based upon an orientation of the mobile wireless communications device.

\* \* \* \* \*